US 6,684,276 B2

(12) United States Patent
Walker et al.

(10) Patent No.: US 6,684,276 B2
(45) Date of Patent: Jan. 27, 2004

(54) PATIENT ENCOUNTER ELECTRONIC MEDICAL RECORD SYSTEM, METHOD, AND COMPUTER PRODUCT

(76) Inventors: Thomas M. Walker, Commonwealth Ortho. & Rehab. 1850 Town Center, Parkway, Suite 400, Reston, VA (US) 20190; Mark Madden, Commonwealth Ortho. & Rehab. 1850 Town Center, Parkway, Suite 400, Reston, VA (US) 20190

( * ) Notice: Subject to any disclaimer, the term of this patent is extended or adjusted under 35 U.S.C. 154(b) by 379 days.

(21) Appl. No.: 09/818,832

(22) Filed: Mar. 28, 2001

(65) Prior Publication Data

US 2002/0170565 A1 Nov. 21, 2002

(51) Int. Cl.[7] ............................................... G06F 13/12
(52) U.S. Cl. ............................... 710/73; 710/18; 705/3; 705/17
(58) Field of Search ................... 710/7, 12, 18, 710/29, 72, 73, 1; 712/225; 705/3, 17, 21, 2, 6; 707/104

(56) References Cited

U.S. PATENT DOCUMENTS

| | | | |
|---|---|---|---|
| 5,255,187 A | | 10/1993 | Sorensen |
| 5,812,984 A | | 9/1998 | Goltra |
| 5,823,949 A | | 10/1998 | Goltra |
| 5,832,450 A | * | 11/1998 | Myers et al. ............ 705/3 |
| 5,924,074 A | | 7/1999 | Evans |
| 5,935,060 A | | 8/1999 | Iliff |
| 5,950,168 A | | 9/1999 | Simborg et al. |
| 5,970,463 A | * | 10/1999 | Cave et al. ............ 705/3 |
| 5,974,389 A | | 10/1999 | Clark et al. |
| 6,026,363 A | * | 2/2000 | Shepard ............ 705/3 |
| 6,064,671 A | * | 5/2000 | Killian ............ 370/389 |
| 6,081,809 A | * | 6/2000 | Kumagai ............ 707/104 |
| 6,113,540 A | | 9/2000 | Iliff |
| 6,154,750 A | * | 11/2000 | Roberge et al. ............ 707/104 |
| 6,272,470 B1 | * | 8/2001 | Teshima ............ 705/3 |
| 6,338,039 B1 | * | 1/2002 | Lonski et al. ............ 705/3 |

OTHER PUBLICATIONS

"Computer Speech Recognition in Psychiatry," by John S. Leipsic, M.D., Psychiatric Times, Aug. 1998, vol. XV, Issue 8.
"Acuity Screen," www.erchoice.com, ER Records, Inc. Copyright 1999, Revised Aug. 22, 2000, 2 pages.
"Active Patient Screen," www.erchoice.com, ER Records, Inc. Copyright 1999, Revised Aug. 22, 2000, 1 page.
MedTech USA Medical Software to Expand Your Knowledge, DiagnosisPro, Comprehensive Classification of Fractures: The Long Bones, 2 pages.
Doctors, 5GL–Doctor (Medical Edition), www.shareware–australia.com/lisa/5glmedical.htm, 10 pages.

* cited by examiner

*Primary Examiner*—Kim Huynh
*Assistant Examiner*—RiJue Mai
(74) *Attorney, Agent, or Firm*—Oblon, Spivak, McClelland, Maier & Neustadt, P.C.

(57) ABSTRACT

A patient encounter electronic medical record system, method, and computer product includes pre-populated, diagnosis specific templates, selective, specialty-specific master databases, and anatomic specific databases and templates to achieve comprehensive, accurate and compliant medical documentation that captures patient data concurrently with the clinical patient encounter session. The system is enabled for a distributed computing environment including graphical user interfaces and voice, text, and digital image and x-ray input.

43 Claims, 29 Drawing Sheets

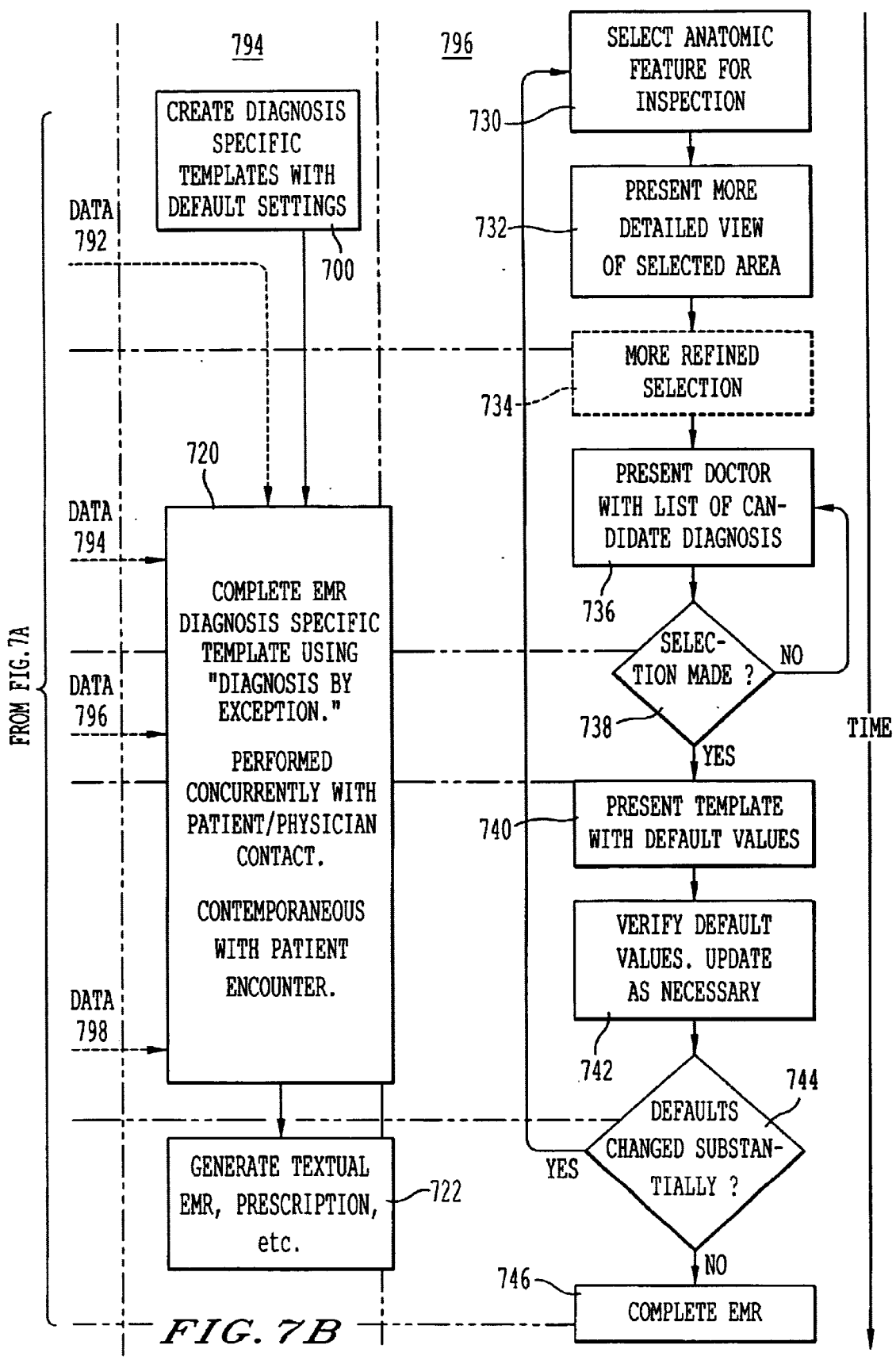

KNEE P.E.
MEDIAL MENISCUS TEAR ACUTE
(POSITIVE FINDINGS ONLY)
INSPECTION —— 12210
12208 —— Color --- Normal
         Abnormal --- Slight / Moderate / Severe
                            Ecchymosis
                            Erythema
                            Palor
                            Plethora
                            Cyanosis
12222 —— Clinical Deformity --- no
                Ant / Post / Med / Lat
                Mild / Mod / Severe —— 12226
12234 —— Athrophy (No, Mild, Moderate, Marked)
         Swelling -- No
                Localized
                Mild / Mod / Severe
                         Ant / Post / Med / Lat
12250 —— Diffuse
                Slight / Mod / Marked
                         Ant / Post / Med / Lat
         Prepateller Bursa
         Infrapateller Bursa
         Pes Anserine Bursa
         Popliitial Space
         Calf (hx) (pe) (rad) (diag) (plan) (report)

*FIG. 12B*

PASSIVE ROM
Normal
Decreased - - - Slightly / Moderately / Markedly
         WITH - - Mild / Moderate / Marked
              PAIN
         WITHOUT pain
         WITH crepitance
              EXT _____ Degrees - - -
(-10) 0 10 20 30 40 50 60 70 80 90 100 110 120 130 140
              FLEX _____ Degrees - - -
       0 10 20 30 40 50 60 70 80 90 100 110 120 130 140
                                          150 160 170

MC MURRAY'S TEST
   NEGATIVE
   POSITIVE — WITH PAIN BUT NO CLICK
            — WITH PAIN AND A CLICK

INSTABILITY
   No
   Mild  /  Mod  /  Marked
   ANTERIOR
      * Lachman Test        (+) / (-) / (+/-)
      * Anterior Drawer Sign (+) / (-) / (+/-)
      * Pivot Shift Test    (+) / (-) / (+/-)
   POSTERIOR
      * Posterior drawer - - - (+) / (-) / (+/-)
      * Sag Sign           (+) / (-) / (+/-)
   LATERAL
   MEDIAL (hx) (pe) (rad) (diag) (plan) (report)

FIG. 12D

Crepitance - - - No
　　　　　　Mild / Mod / Marked
　　　　　　　　　　Subcutaneous
　　　　　　　　　　Deep　　Size_____ Diameter_____

Adenopathy - - - NO
　　　　　　　Yes — groin
Popliteal cyst -- no
　　　　　　- small / medium / large
Popliteal aneurysm -- no
　　　　　　- small / medium / large
Phlebitis - - No tenderness, calor, cords or significant swelling
　　Calf,
　　Medial Thigh
　　Homan's Test - negative
　　　　　　　　- positive RANGE OF MOTION
　ACTIVE and PASSIVE ROM - - Normal
　ACTIVE ROM
　　Normal
　　Decreased - - - Slightly / Moderately / Markedly
　　　WITH pain - - Mild / Moderate / Marked
　　　WITHOUT pain
　　　WITH crepitance EXT_____ Degrees - - -
(-10)  0  10  20  30  40  50  60  70  80  90  100  110  120  130  140

FLEX_____ Degrees
　　　0  10  20  30  40  50  60  70  80  90  100  110  120  130  140
　　　　　　　　　　　　　　　　　　　　140  150  160  170

(hx) (pe) (rad) (diag) (plan) (report)

FIG. 12E

TEXT SUMMARY
13102 — PRESENT HISTORY
MEDIAL MENISCUS TEAR

THIS IS A 25 YR. OLD, CAUCASIAN MAN, WHO SUSTAINED A SPORTS INJURY TO HIS RIGHT KNEE WHEN HE FELL AND TWISTED IT PLAYING SOCCER 5 DAYS AGO. —13122— HE HAD IMMEDIATE PAIN OVER THE MEDIAL JOINT LINE. NO POP OR SNAP WAS NOTED. HE NOTED MILD SWELLING OF SLOW ONSET. HE IS UNABLE TO FULLY FLEX OR EXTEND THE KNEE. THE PAIN HAS SINCE BEEN CONSTANT. NO ECCHYMOSIS, ERYTHEMA, NUMBNESS, BUCKLING, GRINDING OR CALF PAIN HAVE BEEN NOTED. HIS PAIN IS GETTING WORSE. HE FEELS BETTER WITH ICE, REST, KNEE FLEXION, AND IBUPROFEN. HIS PAIN IS MADE WORSE WITH ACTIVITY, KNEE EXTENSION, TWISTING, SQUATTING, AND RUNNING. HE IS UNABLE TO PARTICIPATE IN SPORTS AND IS LIMITED IN ACTIVITIES OF DAILY LIVING. HE HAS MISSED 3 DAYS OF WORK DUE TO THE INJURY.

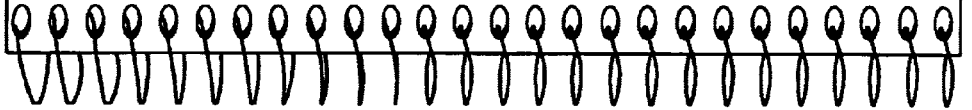

(hx) (pe) (rad) (diag) (plan) (report)

FIG. 13A

PHYSICAL EXAM:
MEDIAL MENISCUS TEAR - ACUTE
TEXT

13210

13218

13214 — INSPECTION REVEALED NORMAL SKIN COLOR WITH NO
CLINICAL DEFORMITY OR ATROPHY. THERE WAS MODERATE,
13220 — DIFFUSE SWELLING. A MODERATE EFFUSION WAS PRESENT.
PALPATION REVEALED MARKED, TRIGGER TENDERNESS
OVER THE MEDIAL JOINT LINE. NO COLOR, MASSES,
CREPITANCE, ADNOPATHY, POPLITEAL CYSTS, ANEURYSMS
OR PHLEBITIS WAS NOTED.
ACTIVE AND PASSIVE MOTION WAS DECREASED
SLIGHTLY WITH MODERATE PAIN. MCMURRAYS TEST WAS
POSITIVE FOR MEDIAL PAIN BUT NO CLICK. NO INSTABILITY
WAS NOTED.
LACHMAN TEST, ANTERIOR DRAWER, POSTERIOR
DRAWER, PIVOT SHIFT AND SAG SIGN WERE NEGATIVE.
NEUROLOGICAL EXAM SHOWED NORMAL MOTOR.
SENSORY, AND REFLEXES. VASCULAR EXAM SHOWED NORMAL
DORSALIS PEDIS AND POSTERIOR TIBIAL PULSES.

(hx) (pe) (rad) (diag) (plan) (report)

FIG. 13B

KNEE : NORMAL (AGE < 15 YRS)

LATERAL, SUNRISE AND STANDING ANT/POST X-RAYS OF THE RIGHT KNEE TAKEN TODAY IN THE OFFICE AND INTERPRETED BY ME SHOW NO ACUTE OR CHRONIC CHANGES. THE JOINT SPACES ARE WELL PRESERVED; NO OSTEOPHYTES ARE NOTED; MINERALIZATION IS GOOD; NO OSTEOCHONDRAL DEFECTS ARE NOTED; PATELLAR ALIGNMENT IS SATISFACTORY. PHYSES ARE PATENT AND APPEAR NORMAL

SIG. _____

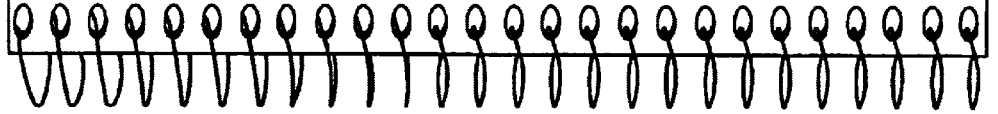

(hx) (pe) (rad) (diag) (plan) (report)

*FIG. 14*

KNEE : AGE > 65 YRS
MILD DJD MEDIAL

LATERAL, SUNRISE AND STANDING ANT/POST X-RAYS OF THE RIGHT KNEE TAKEN TODAY IN THE OFFICE AND INTERPRETED BY ME SHOW NO ACUTE CHANGES. THE MEDIAL JOINT SPACE IS SLIGHTLY NARROW AND MAY SHOW SLIGHT SUBCHONDRAL SCLEROSIS. THE OTHER JOINT SPACES ARE WELL PRESERVED; NO OSTEOPHYTES ARE NOTED; MINERALIZATION IS GOOD; NO OSTEOCHONDRAL DEFECTS ARE NOTED; PATELLAR ASSIGNMENT IS SATISFACTORY.

SIG. _____

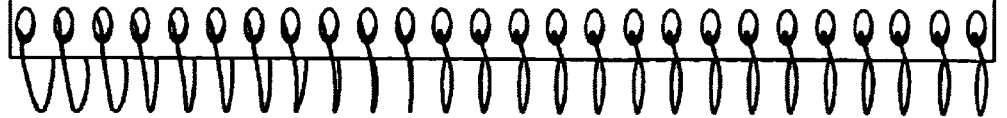

FIG. 15

OUTSIDE X-RAYS WITH PATIENT :
NORMAL

THE PATIENT BRINGS X-RAYS OF THE RIGHT KNEE TAKEN _____, IN ANT/POST, LATERAL AND OBLIQUE VIEWS. THEY ARE REVIEWED BY ME WITH THE PATIENT. THEY SHOW NO ACUTE OR CHRONIC CHANGES. THE JOINT SPACES ARE WELL PRESERVED; NO OSTEOPHYTES ARE NOTED; MINERALIZATION IS GOOD; NO OSTEOCHONDRAL DEFECTS ARE NOTED. A SUNRISE VIEW IS TAKEN TODAY WHICH I FEEL SHOWS THAT PATELLAR ALIGNMENT IS SATISFACTORY.

SIG. _____

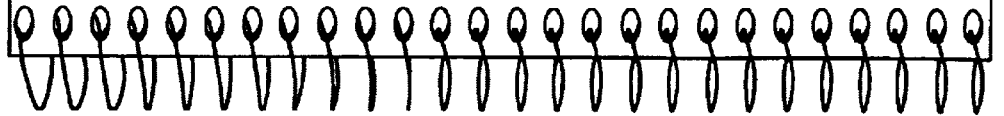

(hx) (pe) (rad) (diag) (plan) (report)

1902 —— SUMMARY TEXT H.P.I. + P.E.
1904 —— MEDIAL MENISCUS TEAR — ACUTE

PATENT NAME: CHASE LOUNGE
DATE OF CONSULTATION: 12/12/00
REFERRING PHYSICIAN: NAUGA HYDE, MD

1920
—— THIS IS A 25 YR. OLD, CAUCASIAN MAN, WHO SUSTAINED A SPORTS INJURY TO HIS RIGHT KNEE WHEN HE FELL AND TWISTED IT PLAYING SOCCER 5 DAYS AGO.

HE HAD IMMEDIATE PAIN OVER THE MEDIAL JOINT LINE. NO POP OR SNAP WAS NOTED. HE NOTED MILD SWELLING OF SLOW ONSET. HE IS UNABLE TO FULLY FLEX OR EXTEND THE KNEE. THE PAIN HAS SINCE BEEN CONSTANT. NO ECCHYMOSIS, ERYTHEMA, NUMBNESS, BUCKLING, GRINDING OR CALF PAIN HAVE BEEN NOTED. HIS PAIN IS GETTING WORSE.

HE FEELS BETTER WITH ICE, REST, KNE FLEXION, AND IBUPROFEN. HIS PAIN IS MADE WORSE WITH ACTIVITY, KNEE EXTENSION, TWISTING, SQUATTING, AND RUNNING. HE IS UNABLE TO PARTICIPATE IN SPORTS AND IS LIMITED IN ACTIVITIES OF DAILY LIVING. HE HAS MISSED 3 DAYS OF WORK DUE TO THE INJURY.

INSPECTION REVEALED NORMAL SKIN COLOR WITH NO CLINICAL DEFORMITY OR ATROPHY. THERE WAS MODERATE, DIFFUSE SWELLING. A MODERATE EFFUSION WAS PRESENT.

PALPATION REVEALED MARKED, TRIGGER TENDERNESS OVER THE MEDIAL JOINT LINE. NO CALOR, MASSES, CREPITANCE, ADENOPATHY, POPLITEAL SYSTS, ANEURYSMS OR PHLEBITIS WAS NOTED.

ACTIVE AND PASSIVE MOTION WAS DECREASED SLIGHTLY WITH MODERATE PAIN. MCMURRAYS TEST WAS POSITIVE FOR MEDIAL PAIN BUT NO CLICK. NO INSTABILITY WAS NOTED.

LACHMAN TEST, ANTERIOR DRAWER, POSTERIOR DRAWER, PIVOT SHIFT AND SAG SIGN WERE NEGATIVE.

*FIG. 19A*

NEUROLOGIC EXAM SHOWED NORMAL, MOTOR, SENSORY, AND REFLEXES. VASCULAR EXAM SHOWED NORMAL DORSAL PEDIS AND POSTERIOR TIBIAL PULSES.

X-RAYS RIGHT KNEE:

LATERAL, SUNRISE AND STANDING ANT/POST X-RAYS OF THE RIGHT KNEE TAKEN TODAY IN THE OFFICE AND INTERPRETED BY ME SHOW NO ACUTE OR CHRONIC CHANGES. THE JOINT SPACES ARE WELL PRESESRVED; NO OSTEOPHYTES ARE NOTED; MINIRALIZATION IS GOOD; NO OSTEOCHONDRAL DEFECTS ARE NOTED; PATELLAR ALIGNMENT IS SATISFACTORY.

SIG. _____

DIAGNOSTIC IMPRESSION:   TORN MEDIAL MENISCUS, RIGHT KNEE, ACUTE (ICD-9 CODE 836.0)

DIAGNOSTIC STUDIES: MRI

TREATMENT PLAN:

REST, ICE AND ELEVATION
CRUTCHES AS NEEDED – CRUTCHES PROVIDED
KNEE SUPPORT – COMPRESSIVE
NSAID – ALEVE

REPORT TO PCP
OFU AFTER MRI

SIG. _____

*FIG. 19B*

PATIENT ENCOUNTER ELECTRONIC MEDICAL RECORD SYSTEM, METHOD, AND COMPUTER PRODUCT

BACKGROUND OF THE INVENTION

1. Field of the Invention

This invention relates generally to systems, methods, and computer products for clinical information capture and management and specifically to systems and processes by which electronic medical records may be created and modified in the clinical environment of a patient encounter.

2. Discussion of the Background

An average patient load for a medical specialist such as an orthopaedic surgeon is twenty patients per half day.

In order for physicians to be paid, insurance companies require the physicians to prepare specific individualized documentation for each patient. The guidelines and requirements for this documentation are strict, and significant financial and criminal penalties are possible if these guidelines are not followed. One set of guidelines is the Health Care Finance Administration guidelines (HCFA), which requires that a complete history be gathered and recorded on all patients. Medicare auditors reason that if a procedure is not documented, the procedure did not happen. Improper documentation may result in fines and a possible jail term.

Medical record documentation is required to record pertinent facts, findings and observations about an individual's health history, including past and present illnesses, examinations, tests, treatments, and outcomes. The medical record chronologically documents the care of the patient and is an important element contributing to high quality care.

The patient encounter (the interaction between the physician and the patient which occurs, for instance, in a physician's office) may be considered to be divisible into a number of segments: a history taking segment; a physical examination segment; a decision making segment, which includes the differential diagnosis phase, a diagnostic studies phase, a definitive diagnosis phase and a treatment plan phase; a documentation segment, which includes creating a record of the findings, decisions, and recommendations of the patient encounter; and a communication segment which includes sharing the documentation created during the patient encounter including reports, instructions, and requests.

Present systems and methods for capturing the information produced during a patient encounter rely heavily on dictation by the physician. This dictation may take as much as five minutes or more per patient encounter, so that the typical half day clinical session requires at least one hundred minutes of dictation by the physician. This dictation is done either between patient encounters, if there is time available, or at the end of the entire clinical session. In many cases the dictation must be done at the end of a physician's working day, which is sometimes well beyond normal working hours.

The principles of documentation that follow are applicable to all types of medical and surgical services in all settings. For Evaluation and Management (E/M) services, the nature and amount of physician work and documentation varies by type of service, place of service and the patient's status.

The levels of E/M services are based on four types of history (problem focused, expanded problem focused, detailed, and comprehensive). Each type of history includes some or all of the following elements: chief complaint (CC); history of the present illness (HPI); review of systems (ROS); and past family and/or social history (PFSH).

The chief complaint is a concise statement describing the symptom, problem, condition, diagnosis, physician recommended return, or other factor that is the reason for the encounter.

The history of present illness is a chronological description of the development of the patient's present illness from the first sign and/or symptom or from the previous encounter to the present.

A review of systems is an inventory of body systems obtained through a series of questions seeking to identify signs and/or symptoms which the patient may be experiencing or has experienced. For purposes of review of systems, at least the following systems are recognized: constitutional systems (e.g., fever, weight loss); eyes; ears, nose, mouth, throat; cardiovascular; respiratory; gastrointestinal; genital urinary; muscular skeletal; integumentary (skin and/or breast); neurological; psychiatric; endocrine; hematologic/lymphatic; and allergic/immunologic.

The past, family and/or social history consists of a review of three areas: past history (the patient's past experiences with illnesses, operations, injuries, and treatments); family history (a review of medical events in the patient's family, including diseases which may be hereditary or place the patient at risk); and social history (an age appropriate review of past and current activities).

For purposes of examination, the following body areas are recognized: head, including the face; neck; chest, including breasts and axillae; abdomen; genitalia, groin, buttocks; back, including spine; and each extremity.

The extent of examinations performed and documented is dependent on clinical judgement and the nature of the presenting problems. They range from limited examinations of single body areas to general multi-system of complete single organ system examinations.

The levels of evaluation and management services recognize four types of medical decision making (straightforward, low complexity, moderate complexity, and high complexity). Medical decision making refers to the complexity of establishing a diagnosis and/or selecting a management option as measured by the number of diagnoses and/or the number of management options that must be considered; the amount and/or complexity of medical records, diagnostic tests, and/or other information that must be obtained, reviewed and analyzed; and the risk of significant complications, morbidity and/or mortality, as well as comorbidities, associated with the patient's presenting problems, the diagnostic procedures and/or the possible management options.

The number of possible diagnoses and/or the number of management options that must be considered is based on the number and types of problems addressed during the encounter. The complexity of establishing a diagnosis and the management decisions that are made by the physician.

The amount and complexity of data to be reviewed is based on the types of diagnostic testing ordered or reviewed. A decision to obtain and review old medical record and/or obtain history from sources other than the patient increases the amount and complexity of data to be reviewed.

The risk of significant complications, morbidity, and/or mortality is based on the risks associated with the presenting problems, the diagnostic procedures, and the possible management options.

The extent of the history that is required for proper documentation varies according to the patient's presenting problem. Certain conditions require a limited history, while other complaints are more involved and demand a more complete history. A complete history should include the patient's chief complaint and the history of the present illness, a review of systems, and past medical, family, and/or social history. If a review of systems and/or a past medical, family, and/or social history have been documented earlier, the physician does not need to repeat this information. However, he or she should indicate that the previous information was reviewed and then updated, if appropriate. A review of systems and the past medical, family, and/or social history may be completed by ancillary staff or the patient. The record should include a note by the physician confirming the information that was documented by others and supplementing, as appropriate.

The type of physical examination that is performed depends upon the patient's presenting problem and the physician's clinical judgement. The examination may be limited to the affected area, or it may involve an entire organ system. The examination can be more extensive by detailing a complete multi-system examination. The guidelines defined 7 body areas and 12 organ systems for the purpose of physical examination.

The guidelines state that the medical record for a comprehensive, multi-system examination must contain the appropriate elements for at least 8 of the 12 organ systems noted. The guidelines do not require a complete examination of each of the organ systems involved in the examination.

The guidelines also state that specific abnormal and relevant negative findings associated with the affected body area should be documented and described. It is considered insufficient to note "abnormal findings" in the medical record without elaborating on what those findings are.

FIG. 1 is a representation of a productivity flow diagram for a conventional physician/patient encounter. The patient encounter for patient 100 is divided into a history taking segment 120, a physical examination segment 122, an X-ray segment 124, a treatment plan segment 126 and a record segment 128. The history taking segment 120, the physical examination segment 122, and the treatment plan segment 126 requires the physician's presence with the patient. The X-ray segment 124 does not require the physician's presence with the patient, so that during the X-ray segment time, the physician may be attending to another patient.

The record segment 128 is generally done without the patient's presence and requires the physician's complete attention, so during the record segment 128 the physician is not engaged in direct patient care. The record segment is the only portion of the patient encounter that can be eliminated or shortened without decreasing time spent on direct patient care.

As can be seen in FIG. 1, a physician often overlaps patient encounters, so that while patient 100 is having an X-ray taken, the physician is attending patient 102 with the physical examination. Due to emergencies requiring the physician's attention, the time between segments is variable and that the clinical session may be interrupted.

As a result of the conventional productivity work flow just described, the record segment is often required to be postponed until after the clinical session, at the end of the working day, in order for the physician to treat waiting sick and injured patients without intolerable delays.

Clinical information conventionally used for medical diagnosis includes ICD-9 (United States Department of Health and Human Services, National Center for Health Statistics, *International Classification of Diseases*, Ninth Revision, Clinical Modification) codes, epidemiology and demographics data, physical findings data, and epidemiology data. This data may also be used advantageously by the present invention to create a selective, specialty specific master database, as described below.

Pertinent clinical findings for representative diseases may be taken from standard references such as "Ferri's Clinical Advisor," (Ferri, Fred F., *Ferri's Clinical Advisor-Instant Diagnosis and Treatment*, 1$^{st}$ ed., Mosby-Year Book, Inc., 1999) the entire contents of which are hereby incorporated by reference. This standard data, an example of which is shown in Table 1, may be used advantageously to create a selective, specialty specific database, as described below.

TABLE 1—BASIC INFORMATION

Definition

An ankle sprain is an injury to the ligamentous support of the ankle. Most (85%) involve the lateral ligament complex. The anterior inferior tibiofibular (AITF) ligament, deltoid ligament, and interosseous membrane may also be injured. Damage to the tibiofibular syndesmosis is sometimes called a high sprain because of pain above the ankle.

ICD-9-CM Codes 945.00 Sprain, ankle or foot

EPIDEMIOLOGY AND DEMOGRAPHICS

Prevalence 1 case/10,000 people each day

Predominant Sex

Varies according to age and level of physical activity

Physical Findings

Often a history of a "pop"

Variable amounts of tenderness and hemorrhage

Possible abnormal anterior drawer test (pulling the plantar flexed foot forward to determine if there is any abnormal increase in forward movement of the talus in the ankle mortise)

Inversion sprains: tender laterally; syndesmotic injuries: area of tenderness is more anterior and proximal Evaluation of motor function Etiology Lateral injuries usually result from inversion and plantar flexion injuries.

Eversion and rotational forces may injure the deltoid or AITF ligament or the interosseous membrane.

FIGS. 2, 3 and 4 are depictions of conventional diagnostic graphical user interfaces which have been used in home medical diagnostic systems. In these conventional systems the user typically displays a graphic image of the body or parts of the body and by using a pointing device, such as a mouse, can indicate the area of the body which is believed to be injured or part of the body in which the patient is experiencing discomfort. For instance, a patient with a leg injury will display the image of the leg on a computer screen and then further focus the diagnosis on a particular area of the leg where the patient is experiencing the most pain. In conventional systems these actions will then typically bring up more computer screens in which textual information is displayed which is used by the patient to further refine the diagnosis. The end result of this process is a diagnosis of the patient's illness or injury, as well as suggested treatment options.

As recognized by the present inventors, the documentation and communication segments of the patient encounter under the present conventional methods and systems have at least the following drawbacks: they have become onerous for physicians; they are very time consuming; they are frequently performed after hours; they are often incomplete due to time constraints; they usually involve multilayered handling and delays in completion; information is not easily or remotely retrievable; and physicians frequently undercode for fear of government reprisals.

Although various electronic medical record systems currently exist, these systems have serious shortcomings. The present inventors have recognized that some limitations of existing systems are as follows: they are primary care based; they have unacceptable learning curves; they increase, rather than shorten, documentation time; they require additional computer skills; are text based, and have complex navigation schematics, have very expensive initial purchase, setup and maintenance costs; they have tool kits that are complex and are not end user friendly; they do not adequately address the "A" and "P" portions of the "S.O.A.P." encounter model; they have unnecessarily large, non-selective databases; they are financially self-destructive; they are not suitable for multiple site, and multiple service practices; they ask too many irrelevant questions; and they are not self-learning. As a consequence, physicians spend too much time using these conventional tools, thus limiting the practical value of the tools.

SUMMARY OF THE INVENTION

The present inventors have recognized that an improved electronic medical records system includes the following characteristics: it saves physicians time; it has a minimum learning curve; it uses speciality specific databases; it uses simple tool kits, which allow end user modifications; it addresses all portions of the "S.O.A.P." encounter model; the documentation produced integrates patient demographics, clinical information, E/M guidelines, treatment plans, reports, referral letters, prescriptions, coding, and HCFA compliance requirements; and it has reasonable startup and maintenance costs.

Selected features of the inventive system include:

graphics/icon modulated schematics;

selective, speciality-specific, master databases;

anatomic specific, secondary databases and templates;

diagnosis specific, prepopulated templates for E/M documentation, x-rays, diagnostic studies, prescriptions, and reports;

drilldown and rollup logic;

end-user modifiability;

text and voice recognition enablement, at each level of data abstraction;

image capture enablement; and digital x-ray enablement.

Significant efficiencies in the documentation process can be achieved by an innovative application of "bottom-up" reasoning and backward-chaining, proceeding from a diagnostic conclusion to the clinical findings that are most probably linked with the diagnosis. The present inventors have further recognized that an experienced clinical specialist can quickly arrive at a highly probable diagnosis within a few moments of encountering the patient. According to the present invention, this clinical expertise is used to enable efficient documentation production by allowing the physician to use diagnostic specific templates, with pre-populated default values for diagnosis analysis steps, to logically structure the documentation production process. Unnecessary physician input is thereby eliminated, since the default values, which may be overwritten by the physician if appropriate, are already selected, so that the documentation process can be completed concurrently with the patient encounter.

The present invention achieves the following advantages over existing electronic medical record systems.

The present invention saves physicians time.

The present invention eliminates the lengthy data entry process required by current electronic medical record programs.

The present invention eliminates most dictation, multiple reports, written prescriptions for medications, diagnostic studies and physical therapy, the manual completion of forms, and separate sources for patient education materials.

The present invention saves physician staff time.

The present invention eliminates the need for transcription, filing, report composition, and chart retrievals.

The present invention saves the practice money. The present invention decreases staffing requirements, with considerable overhead reduction.

The present invention achieves major savings for software companies by reducing the technical staff needed for system startup and future system support.

The present invention produces complete and thorough documentation that is comprehensive, accurate, and compliant.

The present invention improves patient flow.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 12A–F illustrate an exemplary diagnostic specific template according to the present invention.

FIGS. 13A–B are example textural history/examination/treatment records according to the present invention.

FIGS. 14–17 illustrate exemplary embodiments of the schematic data for x-ray findings relevant to a medial meniscus tear according to the present invention.

FIG. 18 is an exemplary embodiment of the schematic data associated with treatment of a medial meniscus tear according to the present invention.

FIG. 19 illustrates an exemplary embodiment of a summary text history of present illness and physical examination associated with a medial meniscus tear-acute according to the present invention.

DETAILED DESCRIPTION OF THE PREFERRED EMBODIMENTS

Figure 5:
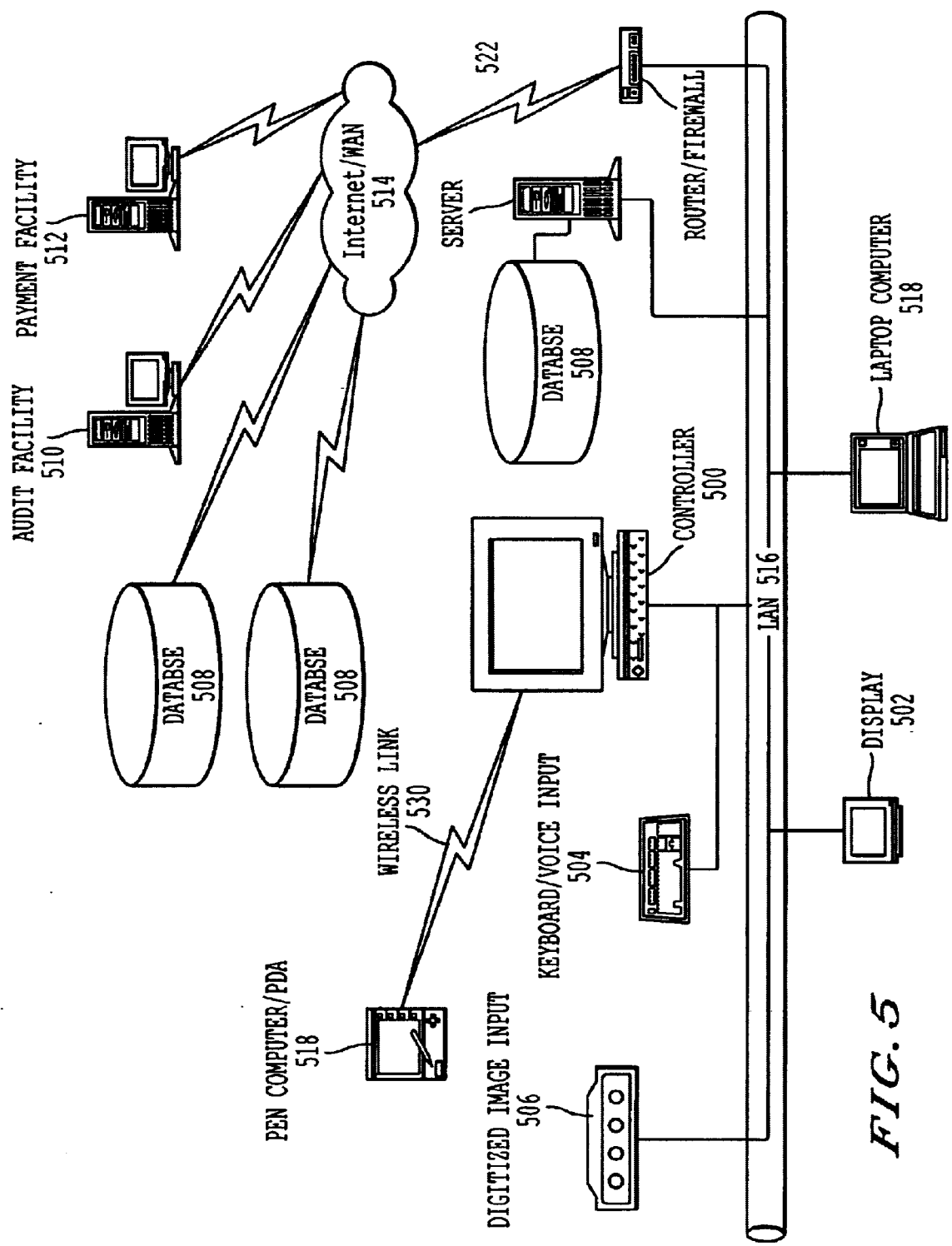
FIG. 5 is a system block diagram according to the present invention.

Referring now to the drawings, wherein like reference numerals designate identical or corresponding parts throughout the several views, and more particularly to FIG. 5 thereof, FIG. 5 is a system block diagram of a preferred embodiment according to the present invention. This system includes a controller 500, a display 502, a keyboard and/or a voice input device 504, and a digitized image input device or channel 506. Communications links 532 connect the display 502 to the keyboard and voice input 504 and digitized image input 506 to the controller 500. The controller 500 may be connected via a communication link 522 to a local area network (LAN) 516. The controller 500 may also be connected to a wide area communications network (WAN) 514. Through the wide area communications network the controller may access remote database 508 as well as audit facility 510 and payment facility 512. The remote database 508 may contain patient data, demographic statistics, and other information pertinent to diagnosis and treatment.

Mobile devices 518, such as handheld mobile telephones with data input facility, or a personal digital assistant (PDA), may be connected via wireless links 530 to communication links 516 and 522. The mobile devices 518 may be used for patient data input while one patient is waiting in the waiting room, or at home before coming to the physician's office.

Figure 6:
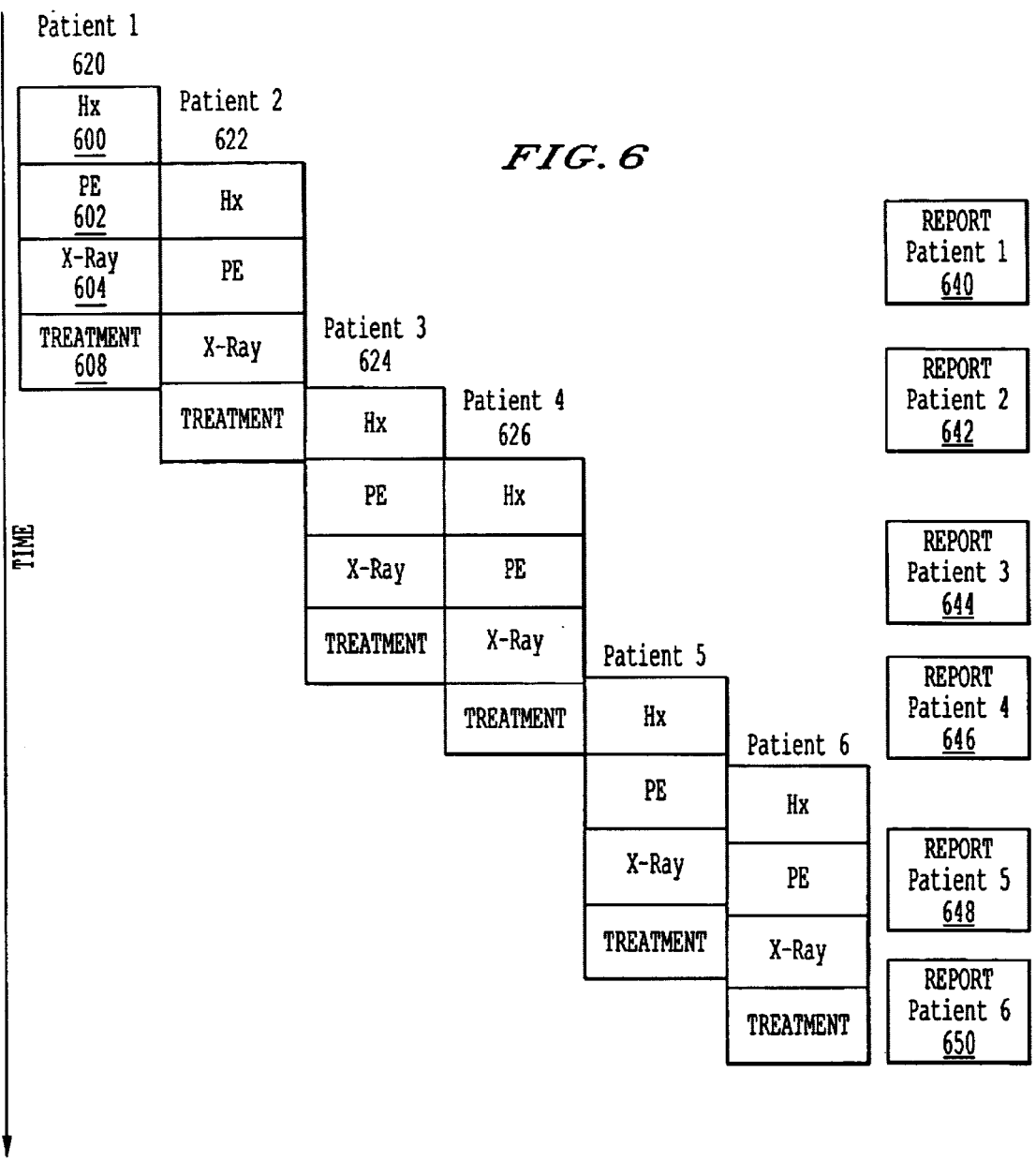
FIG. 6 is a schematic diagram of productivity flow according to the present invention.

FIG. 6 is an exemplary productivity flow diagram according to the present invention. In FIG. 6, no record segment occurs at the end of the patient encounter because the record and documentation process, according to the present invention, occurs concurrently with the history segment 600, the physical examination segment 602, and the treatment segment 608. As is illustrated, reports 640–650 are produced concurrently with the patient encounters.

Figure 7A:
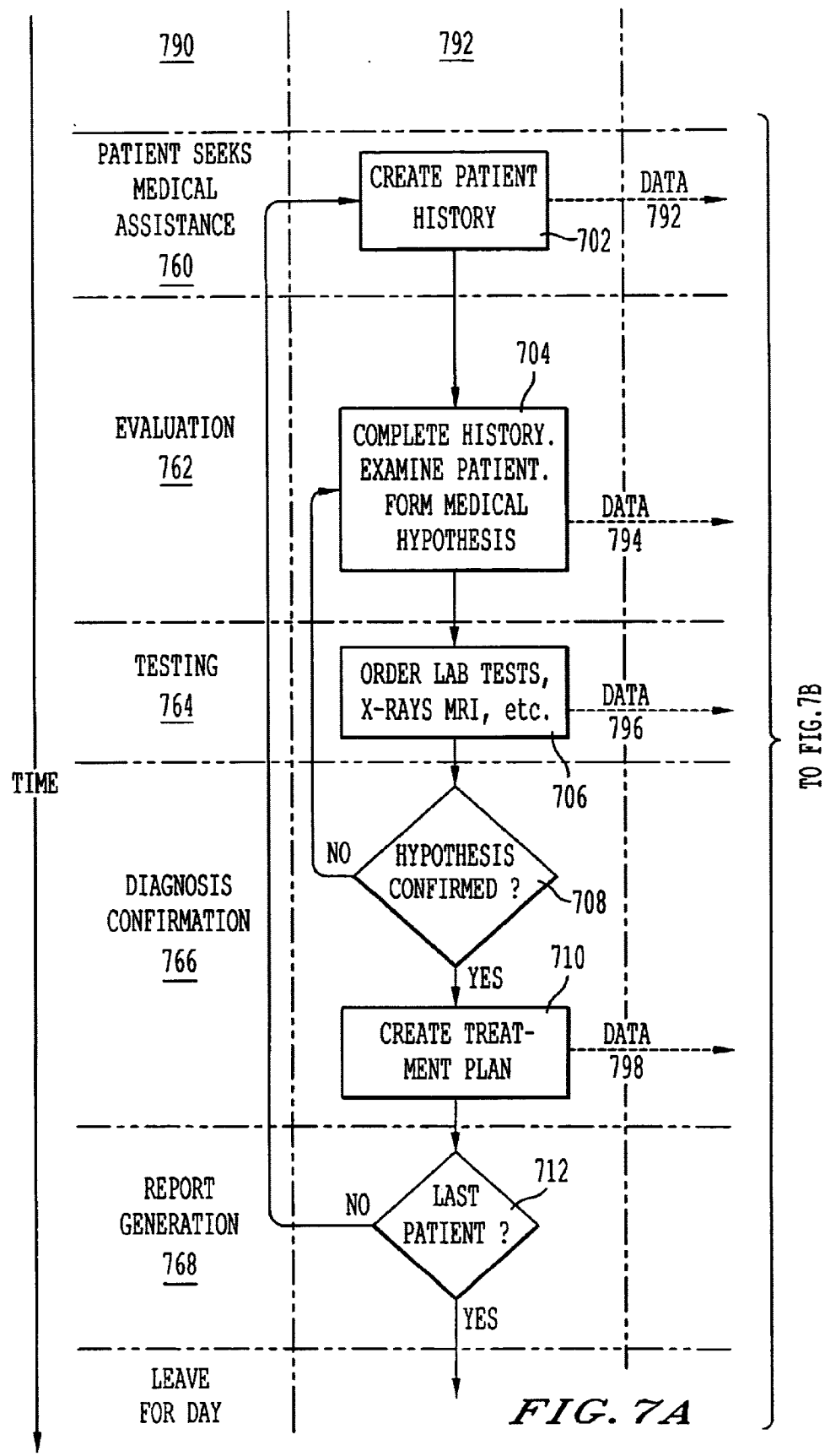
FIG. 7 is a system process flow diagram according to the present invention.

Referring now to FIG. 7, the exemplary system flow is associated with different phases of the medical/clinical process according to the present invention. Before encountering a patient seeking medical attention 760, diagnosis specific templates with default settings 700 are created. The creation of the diagnosis specific templates and their structure will be further discussed below, especially in regard to FIG. 9A. The patient seeking medical assistance 760 triggers the beginning of step 702 in FIG. 7 which is the creation of the patient history. The patient encounter then proceeds to an evaluation phase 762 and possibly a testing phase 764. The patient encounter usually includes a diagnosis confirmation phase 766 and a report generation phase 768. The sequence of phases is then repeated for the next patient. The sequence of phases is shown, for example, in group 790.

Associated with the phases in group 790 are a sequence of physician actions in which the patient is evaluated, a diagnosis is made, and a treatment plan is created. In group 792, for example, the patient history is created 702, often by ancillary personnel such as nurses or other staff, and then the history of the patient is completed by the physician 704.

The physician forms a hypothetical diagnosis which guides the physician during the patient encounter. The hypothetical diagnosis forms the basis for a set of relevant medical questions to be answered by the clinical process.

The physician examines the patient 704, and usually orders medical tests or X-rays 706, and then awaits the results of the lab tests or X-rays. When the lab tests and the X-rays are complete the physician will confirm his hypothetical diagnosis by comparing the results of the lab tests and X-rays with the expected laboratory findings and radiographic findings for the particular diagnosis that the physician has formed. If the diagnosis is not confirmed the physician will order further tests or conduct a more extensive physical examination. If the medical hypothesis is confirmed 708 then the physician will create a treatment plan 710.

For a typical clinical session of one half day this cycle is repeated on average 20 times in the course of evaluating and treating 20 patients.

During each of the steps in group 792, for instance during the creation of the patient history 702, pertinent medical information related to the patient is captured contemporaneously in the electronic medical record system of the present invention. The completion of the electronic medical record of the present invention occurs concurrently with the physician-patient contact during the patient encounter.

For example, during the creation of the patient history, data flows into the electronic medical record system of the present invention through data path 792. Likewise, during the physician's history taking and physical examination of the patient, data flows through data flow path 794 into the electronic medical record system and is captured by the present invention.

Because clinical data flows into the electronic medical record concurrently with the patient encounter, the patient's electronic medical record is essentially complete by the end of the patient encounter.

The completion of the electronic medical record using the present invention advantageously uses the concept of "diagnosis by exception." The present inventors have recognized that many of the problems of conventional systems are caused by repetitious, laborious, and time consuming input of routine findings associated with a particular diagnosis. The present inventors have further recognized that significant improvements in efficiency can be obtained by pre-populating diagnostic specific templates with data that is appropriate to a particular specific diagnosis.

In group 796 of FIG. 7, the process of completing the electronic medical record of the present invention is further illustrated. A preferred embodiment of the present invention includes selecting an anatomic feature for inspection 730. The specific anatomic feature is then refined to a more detailed view 732 and 734 which is appropriate to the diagnosis. The system of the present invention then presents the physician with a list of candidate diagnoses 736 from which the physician selects an appropriate diagnostic specific template 738. When the appropriate template is presented to the physician on, for example, a computer screen with a graphical user interface, the physician then verifies that the default values highlighted in the diagnostic specific template are appropriate for the particular patient's diagnosis and condition 742. The physician determines if the number of default values that have changed is substantial 744, and may then select another anatomic feature which more closely correlates with the patient's particular condition. When the values of the diagnostic specific template are completed in a way which is appropriate to the diagnosis for the particular patient being examined and treated 746, the physician completes the electronic medical record. The steps described 730 to 746 occur contemporaneously with the patient encounter. A textual record or report may be generated after the clinical session is over for the day 722.

Figure 8:
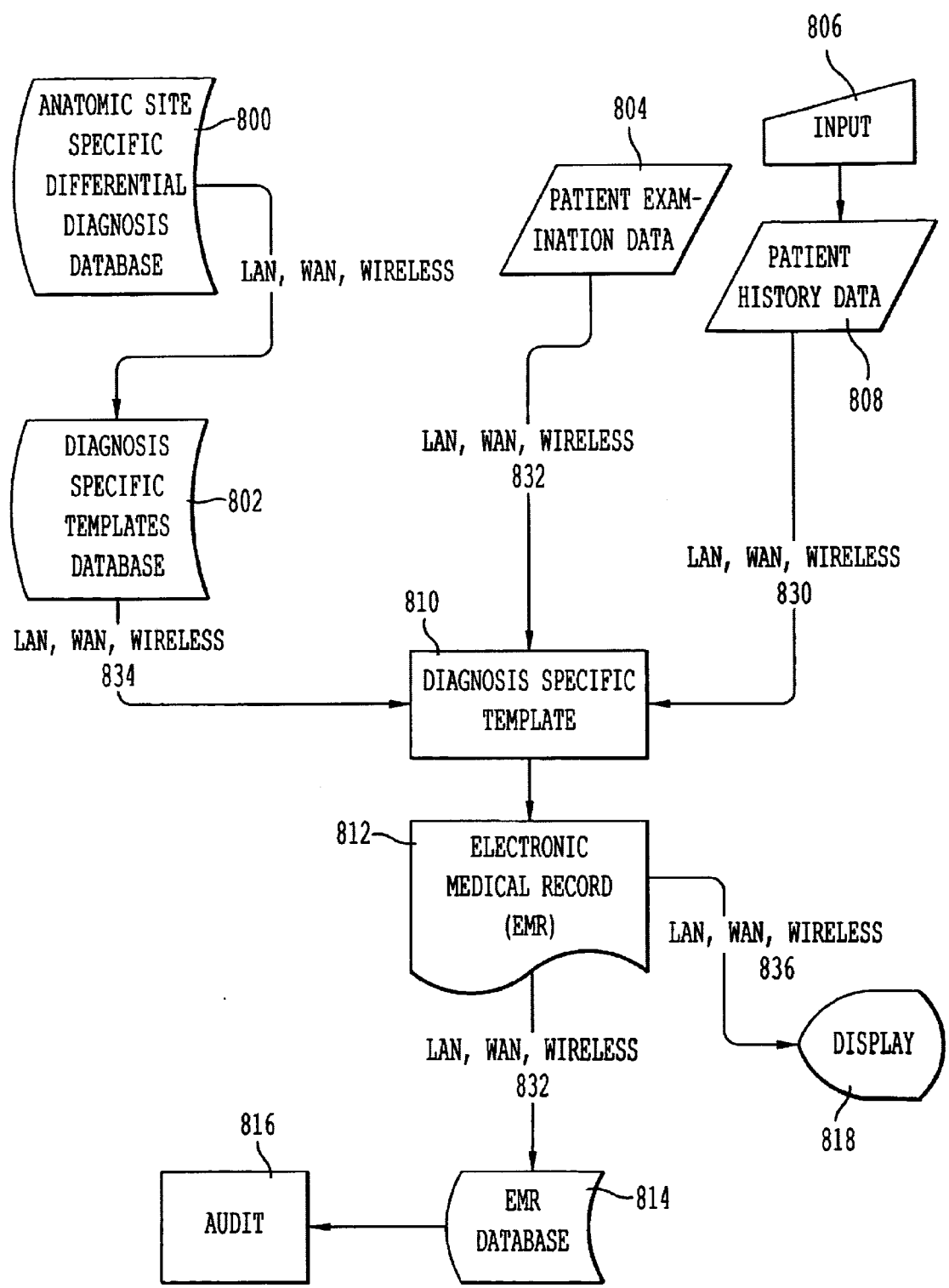
FIG. 8 is a system data flow block diagram according to the present invention.

FIG. 8 shows example data flows 834, 832, and 830 which contribute to the formation of the diagnosis specific template. The computer network architecture of the equipment in FIG. 8 can be distributed client/server architecture that can include a middleware layer such as CORBA or DCE.

The anatomic site specific differential diagnosis database 800 may be a source of demographic data which may be analyzed and used to create the appropriate diagnosis specific template database 802. Patient examination data 804 and patient history data 808 also are sources of data which is used to populate a diagnosis specific template 810.

The diagnosis specific template 810 is the source of data for the electronic medical record 812. Electronic medical record 812 may be transmitted via a LAN, WAN, or wireless network 836 to a display 818 which may be a graphical user interface. In addition, the electronic medical record produced in the preferred embodiment of the present invention may be transmitted via communications link 838 to a database 814. The electronic medical record database 814 may be the source of data for audit facility 816.

Figure 9A:
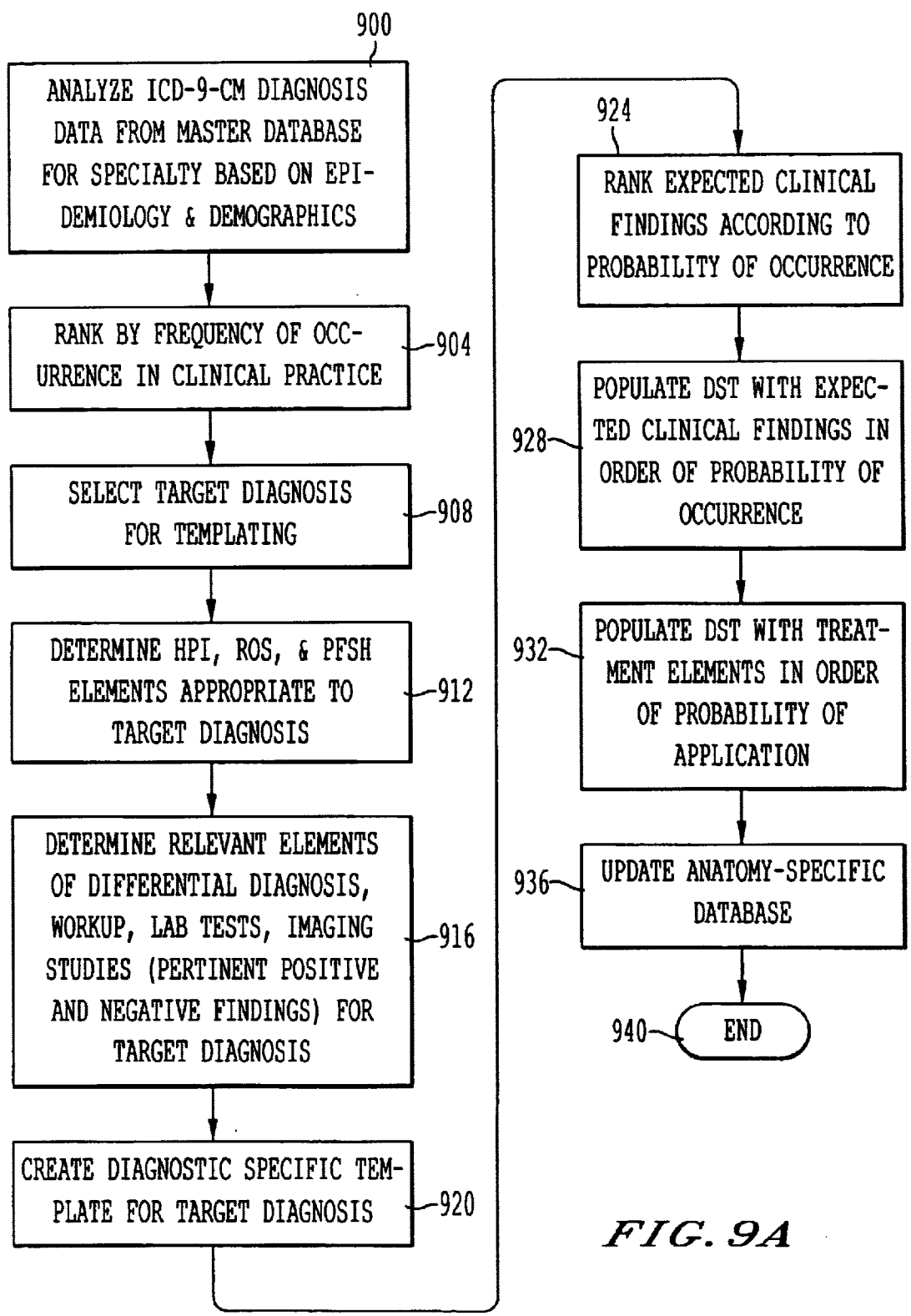
FIG. 9A is a flowchart illustrating diagnostic specific template creation according to the present invention.

FIG. 9A describes a process of creating diagnosis specific templates according to the present invention. In the exemplary embodiment, medical specialists and physicians analyze ICD-9-CM (United States Department of Health and Human Services, National Center for Health Statistics, *International Classification of Diseases*, Ninth Revision, Clinical Modification) diagnosis data from a master database for medical specialities which is based on disease epidemiology and demographics 900, the entire contents of which being incorporated herein by reference.

In the analysis step 900, a database which contains the frequency of occurrence of a large number of diseases is analyzed. The result of this analysis is to produce a profile of the most frequently encountered diseases, in a particular geographic area with a particular population distribution, that can be expected in a medical specialty practice, such as orthopaedics. The ranking by frequency 904 allows the physician to focus on the most important diagnosis that are likely to be encountered in daily practice in his speciality.

Based on the ranking of diseases by frequency the physician will select a subset of the diseases for which diagnosis specific templates will be created. The physician will select a target diagnosis for templating 908.

The physician who is creating the diagnostic specific template will determine the HPI, ROS, and PFSH elements appropriate to the target diagnostic specific template 912. In this step the physician will also select the germane clinical features of the target disease.

The physician creating the diagnostic specific template will determine the relevant elements of a differential diagnosis, as well as work-up data, lab tests, imaging studies, pertinent positive and negative findings for the target diagnosis, and other relevant clinical factors 916.

From all of the relevant data mentioned, the physician creates the diagnostic specific template for the target diagnosis 920.

Based on clinical experience, the physician will then rank the expected clinical findings for the specific diagnosis according to the probability that a particular finding will be associated with a particular diagnosis 924. The physician will then populate the diagnostic specific template with the expected clinical findings in order of their probability of occurrence 928.

The physician creating the diagnostic specific template will populate the diagnostic specific template with the treatment elements appropriate for the treatment of the diagnosed disease in order of probability of application 932.

The newly created diagnostic specific template is then added to the database of anatomic specific templates 936.

According to the present invention, data is structured into hierarchical layers (drilldown layers) from abstract, high-level, coarsely detailed data (anatomical maps of the whole body, for example) down to low-level, highly detailed data (textual clinical reports, for example). The user of the present invention may traverse levels of detail from coarse detail to fine detail quickly and accurately, using, for example, a graphical user interface (GUI). Structuring data as drilldown layers or objects allows important relevant diagnostic specific data to be used efficiently, because unnecessary or irrelevant detail can be hidden.

Figure 9B:
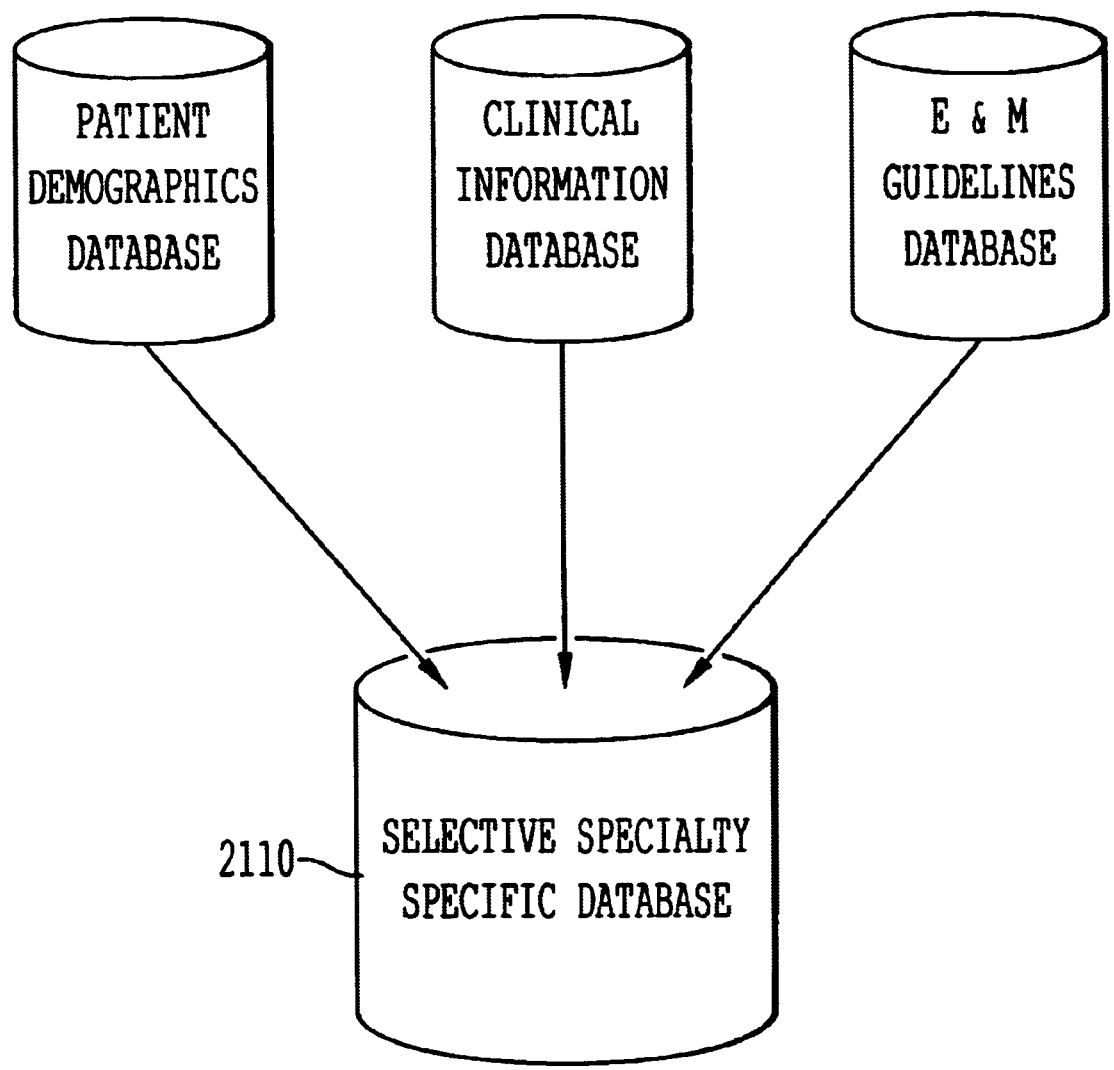
FIG. 9B is a schematic diagram representing the formation of selective, specialty specific databases.

FIG. 9B is a schematic diagram representing the formation of selective, specialty specific databases. An example master database may be formed from patient demographic data, clinical information pertinent to target diseases, and examination and management guidelines. Well known database techniques may be used to analyze and structure data in the selective specialty specific database so that the data may be used efficiently to create anatomic diagnosis specific templates.

Table 1 is the data output table of the exemplary embodiment of the present invention. For example, ICD-9 code is associated with a description "pain knee" and associated with the "number of patients" in the data analysis who experienced the particular problem. The table is arranged in order of frequency of the occurrence of the various diseases and injuries. Based on this data, a specialist may then select the injuries or diseases which is most likely to be encountered in his clinical practice and then create a target anatomic diagnosis specific templates appropriate for these diseases.

TABLE 2

DIAGNOSED CODES BY NUMBER OF PATIENTS

| ICD-9 Code | DESCRIPTION | # OF PATIENTS | % |
|---|---|---|---|
| 715.16 | Osteoarthritis knee | 1111 | 12.04% |
| 717.7 | *Chondromalacia patella* | 840 | 7.38% |
| 719.48 | PAIN KNEE | 547 | 1.93% |
| 726.1 | ROTATOR CUFF/SUPRASPINATUS SYNDROME (NOS) | 487 | 3.55% |
| 726.11 | TENDONITIS SHOULDER | 382 | 2.40% |
| 726.5 | BURSITIS troch/hip/ischiogluteal | 374 | 1.45% |
| 726.32 | EPICONDYLITIS LATERAL | 373 | 2.10% |
| 729.5 | PAIN IN LIMB (ARM, LEG, HAND, FOOT) | 286 | 0.61% |
| 354 | CARPAL TUNNEL SYNDROME | 280 | 2.04% |
| 726.2 | IMPINGEMENT SYNDROME, SHOULDER | 272 | 3.51% |
| 722.52 | DEGENERATIVE DISC DISEASE LUMBAR/LUMBOSA | 253 | 4.04% |
| 719.41 | PAIN SHOULDER | 246 | 1.01% |
| 728.71 | PLANTAR FASCIITIS | 245 | 0.89% |
| 715.15 | OSTEOARTHROSIS HIP | 241 | 4.37% |

Figure 10:
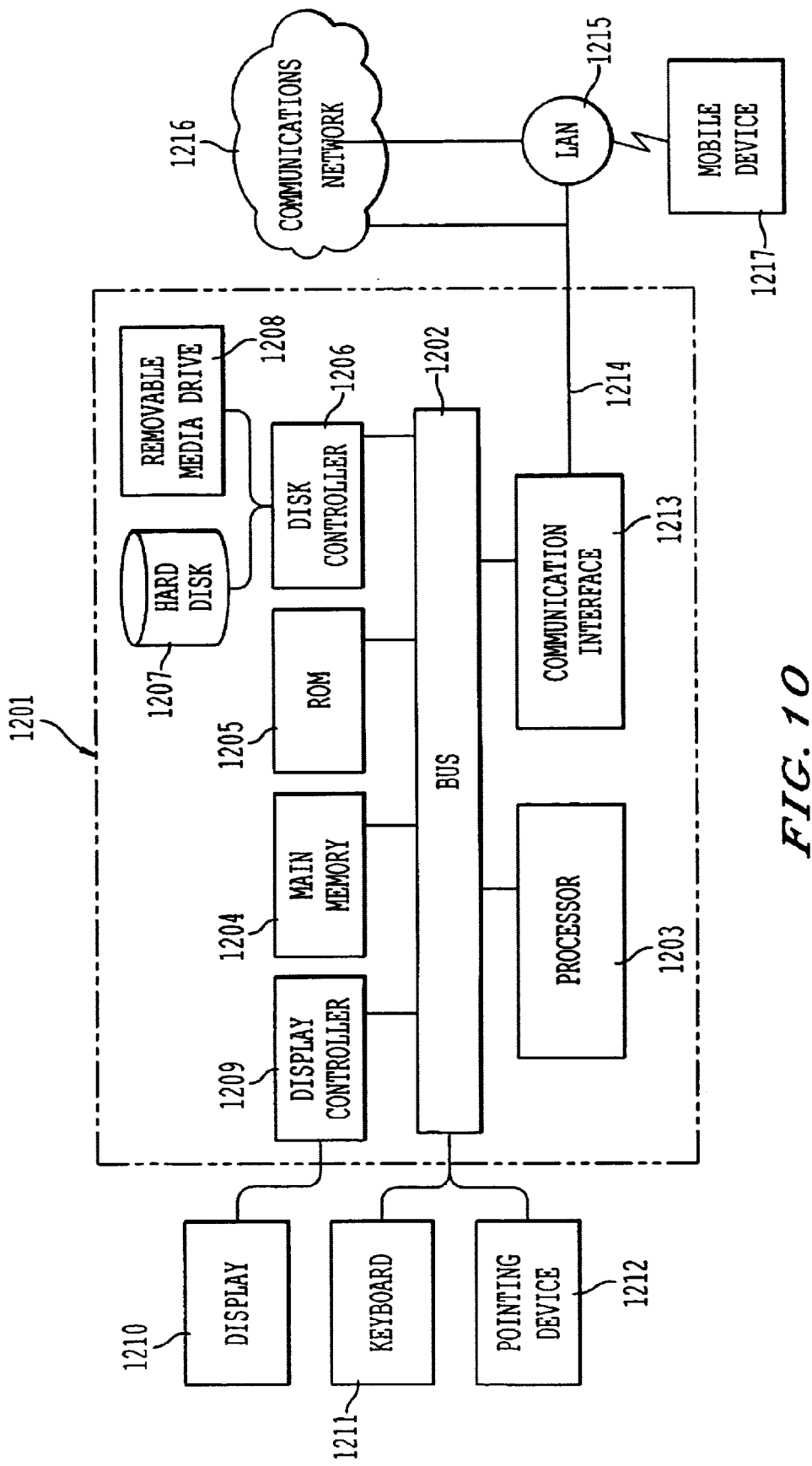
FIG. 10 is a more detailed system block diagram according to the present invention.

FIG. 10 is a more detailed block diagram of a preferred embodiment according to the present invention. FIG. 10 illustrates a computer system 1201 upon which an embodiment of the present invention may be implemented. More detailed descriptions of these components may be found in White, R., *How Computers Work*, Que Corporation, 1999, the entire contents of which being incorporated herein by reference. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable ROM (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

Figure 1:
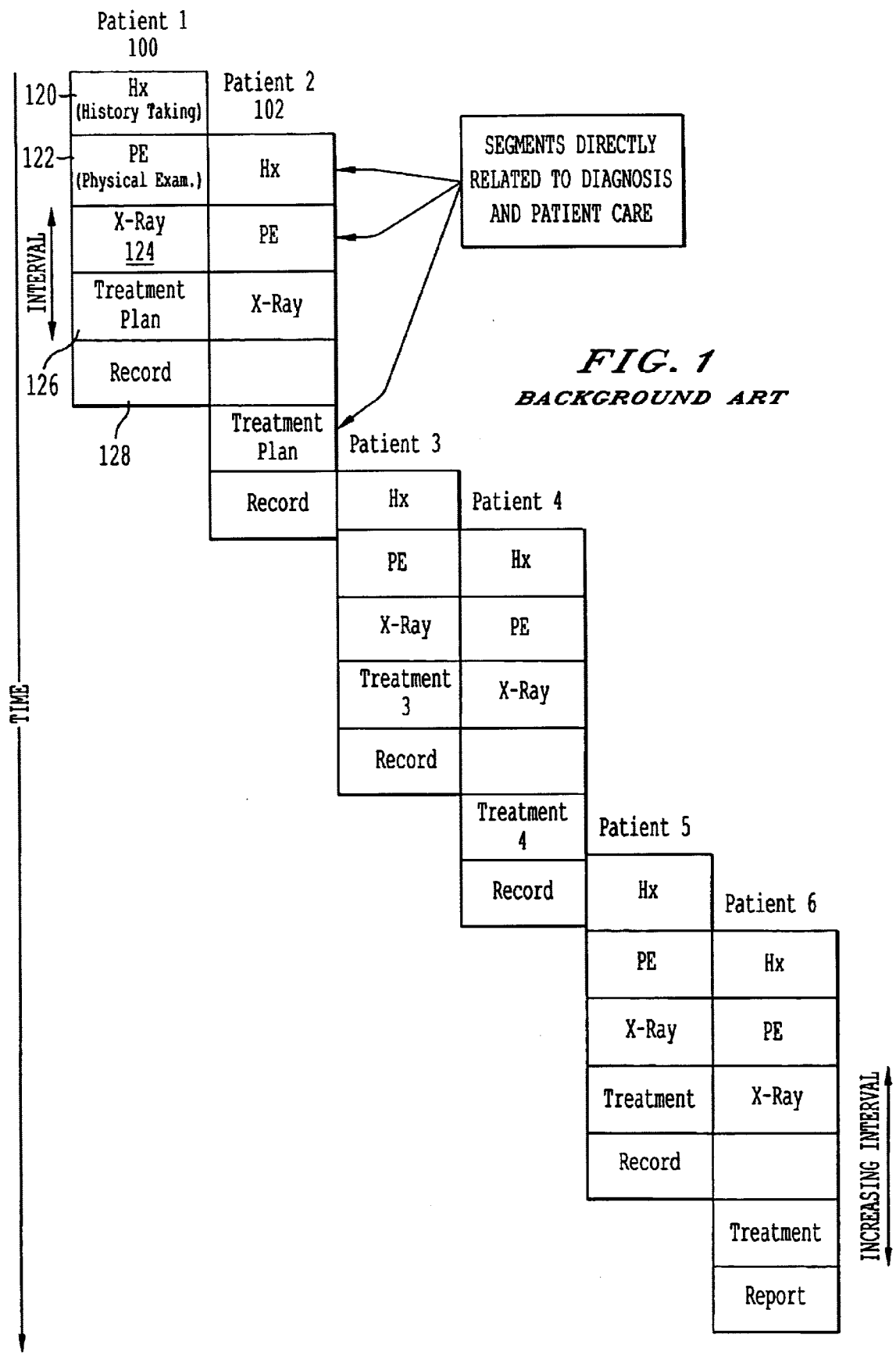
FIG. 1 is a schematic background art productivity flow diagrams.
Figure 2:
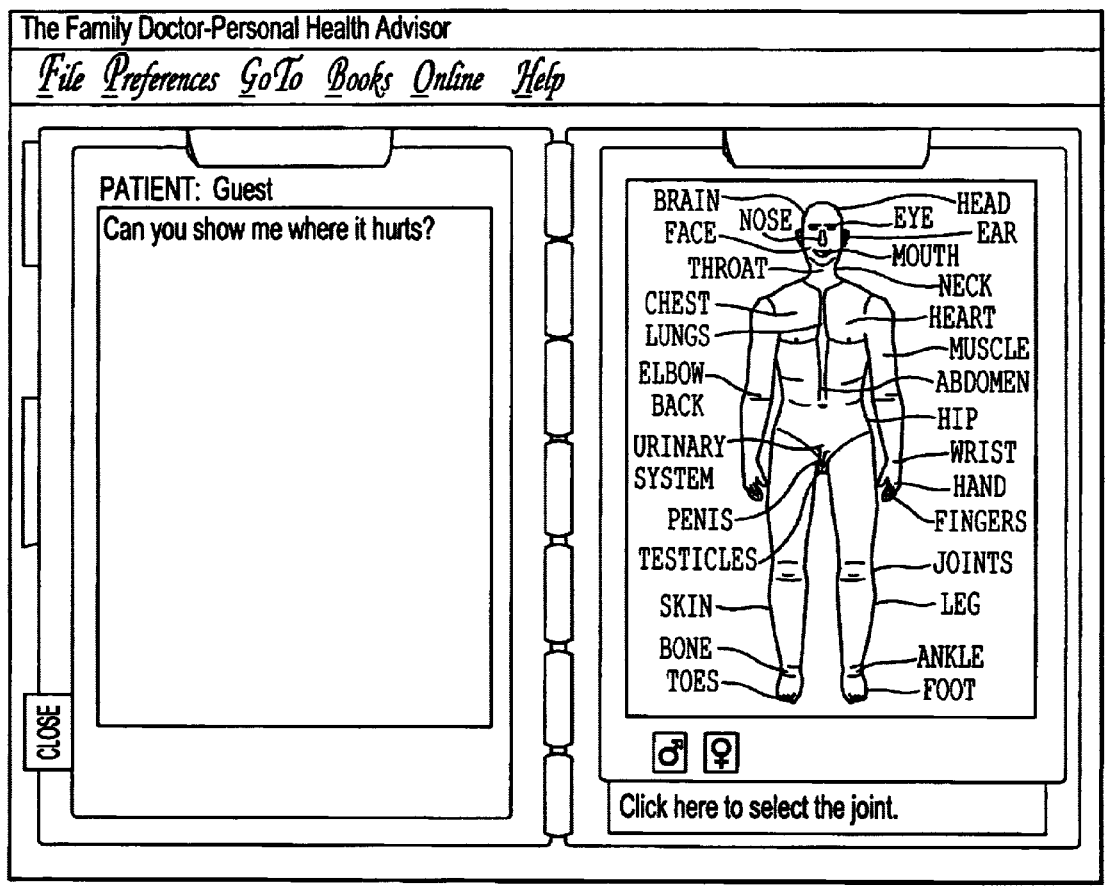
FIG. 2 is a background are representation of the "PERSONAL DOCTOR" graphical user interface for a commercial product.
Figure 3:
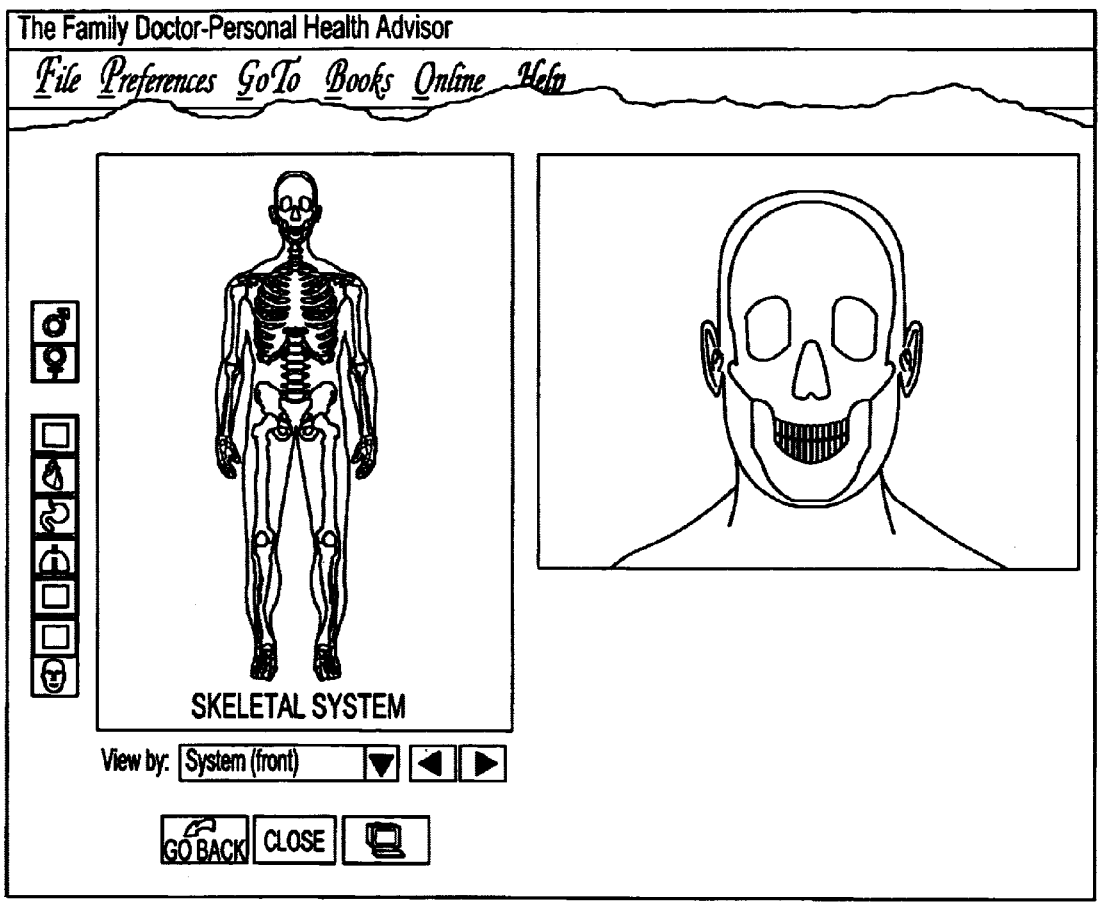
FIG. 3 is a background art depiction of the "PERSONAL DOCTOR" graphical user interface for a commercial product.
Figure 4:
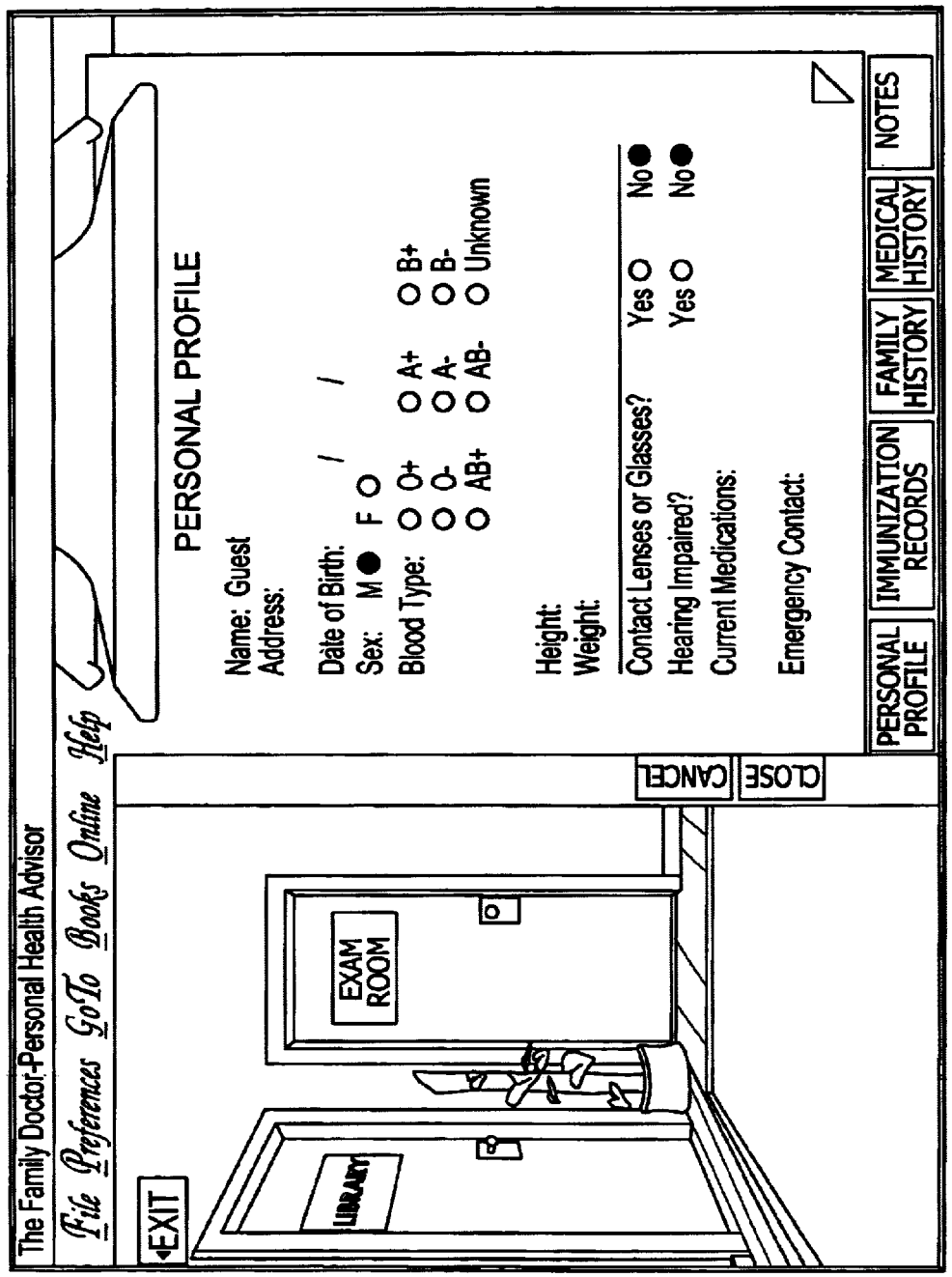
FIG. 4 is a background art depiction of a "PERSONAL DOCTOR" graphical user interface for a commercial product.

The computer system 1201 may also include a display controller 1209 coupled to the bus 1202 to control a display 1210, such as a cathode ray tube (CRT), for displaying information to a computer user. The computer system includes input devices, such as a keyboard 1211 and a pointing device 1212, for interacting with a computer user and providing information to the processor 1203. The pointing device 1212, for example, may be a mouse, a trackball, or a pointing stick for communicating direction information and command selections to the processor 1203 and for controlling cursor movement on the display 1210. In addition, a printer may provide printed listings of the data structures/information shown in FIGS. 3 and 4, or any other data stored and/or generated by the computer system 1201.

The computer system 1201 performs a portion or all of the processing steps of the invention in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 1201, for driving a device or devices for implementing the invention, and for enabling the computer system 1201 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216, as discussed in Gralla, P., *How the Internet Works*, Que, 1999, the entire contents of which being incorporated by reference. In preferred embodiments, the local network 1214 and the communications network 1216 preferably use electrical, electromagnetic, or optical signals that carry digital data streams. The signals through the various networks and the signals on the network link 1214 and through the communication interface 1213, which carry the digital data to and from the computer system 1201, are exemplary forms of carrier waves transporting the information. The computer system 1201 can transmit and receive data, including program code, through the network(s) 1215 and 1216, the network link 1214 and the communication interface 1213. Moreover, the network link 1214 may provide a connection through a LAN 1215 to a mobile device 1217 such as a personal digital assistant (PDA) laptop computer, or cellular telephone. The LAN communications network 1215 and the communications network 1216 both use electrical, electromagnetic or optical signals that carry digital data streams. The signals through the various networks and the signals on the network link 1214 and through the communication interface 1213, which carry the digital data to and from the system 1201, are exemplary forms of carrier waves transporting the information. The processor system 1201 can transmit notifications and receive data, including program code, through the network(s), the network link 1214 and the communication interface 1213.

Figure 11A:
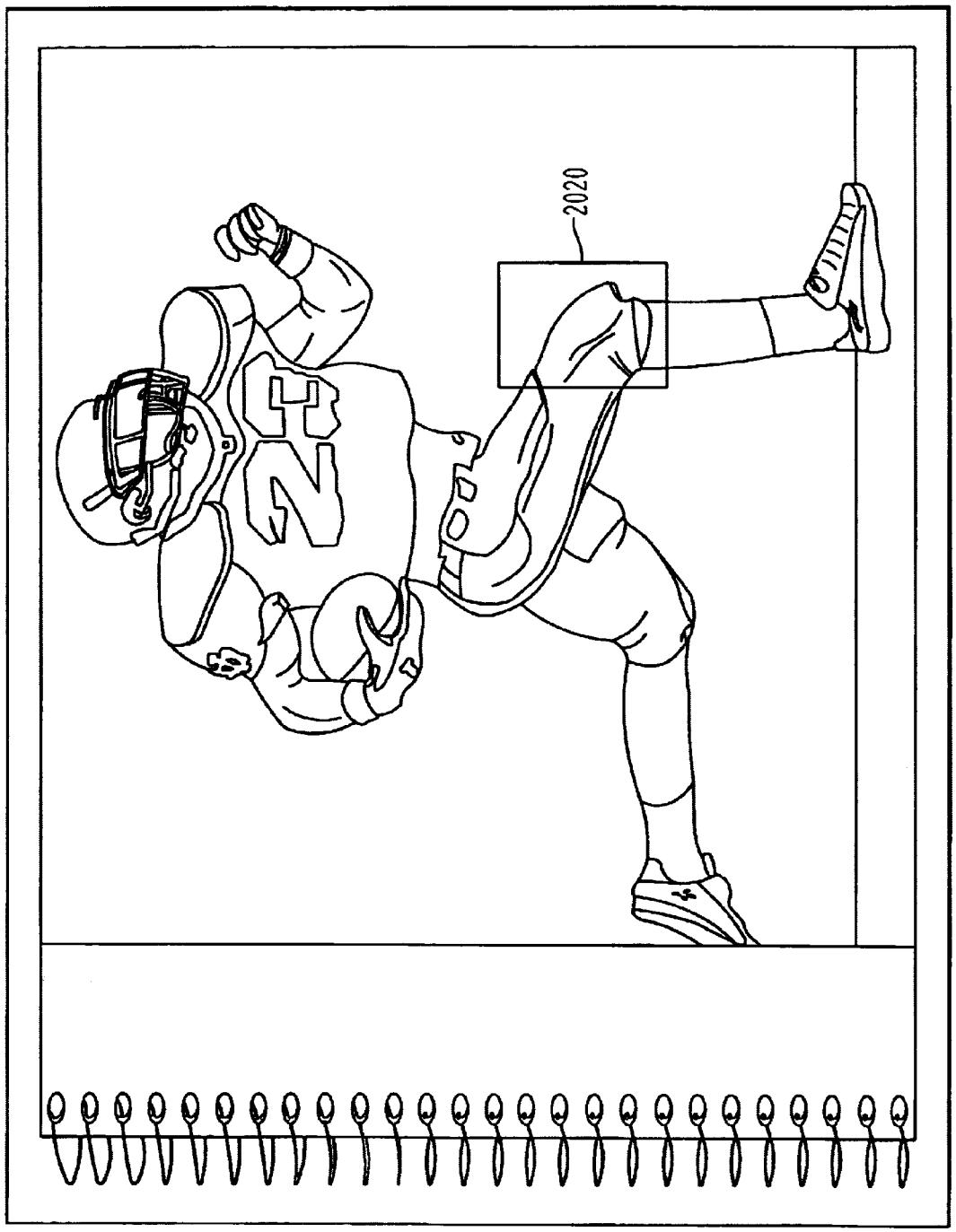
FIGS. 11A–B illustrate an example of the anatomic/diagnostic graphical user interface according to the present invention.

Referring now to FIG. 11A, an example of the drilldown logic feature of the exemplary embodiment of the present invention will now be described. In FIG. 11A, the user of the system is presented with a high level anatomical map of the human body, where the figure depicted reflects appropriate demographic characteristics such as sex, age, activity level, and so forth. The user of the present invention may, for example, use a pointing device to click on a particular area of the high level anatomical map such as 2020. Clicking on the particular area invokes the drilldown logic, which then causes a screen containing more anatomical detail to be displayed.

Figure 11B:
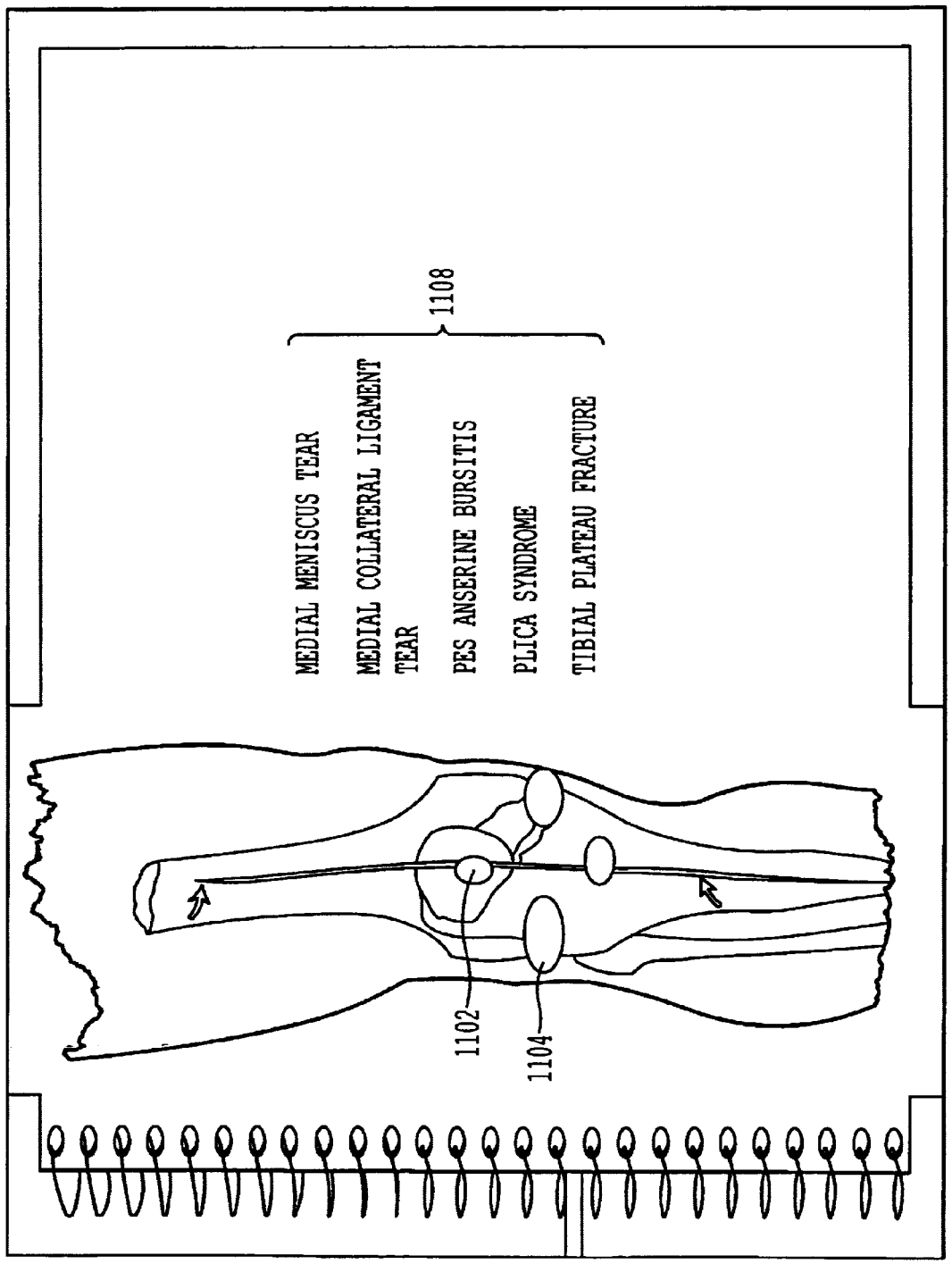

Referring now to FIG. 11B, a drilldown layer containing more detailed anatomical information is displayed. The user may traverse further levels of anatomical detail by selecting the target area with a pointing device and invoking the drilldown logic by clicking on the selected area.

The user of the exemplary embodiment of the present invention may traverse to higher layers containing coarser anatomical detail by invoking roll-up logic.

Referring again to FIG. 11B, an exemplary embodiment of the present invention is depicted schematically where hot spots 1102 and 1104 are located on anatomical features of interest. These hot spots 1102 and 1104 are associated with specific diagnosis appropriate for the anatomical area. The user of the present invention may invoke a data schematic appropriate for a particular injury 1108 by selecting and clicking on a hot spot. This user act will then invoke the appropriate prepopulated diagnosis specific template for the particular area selected.

Figure 12A:
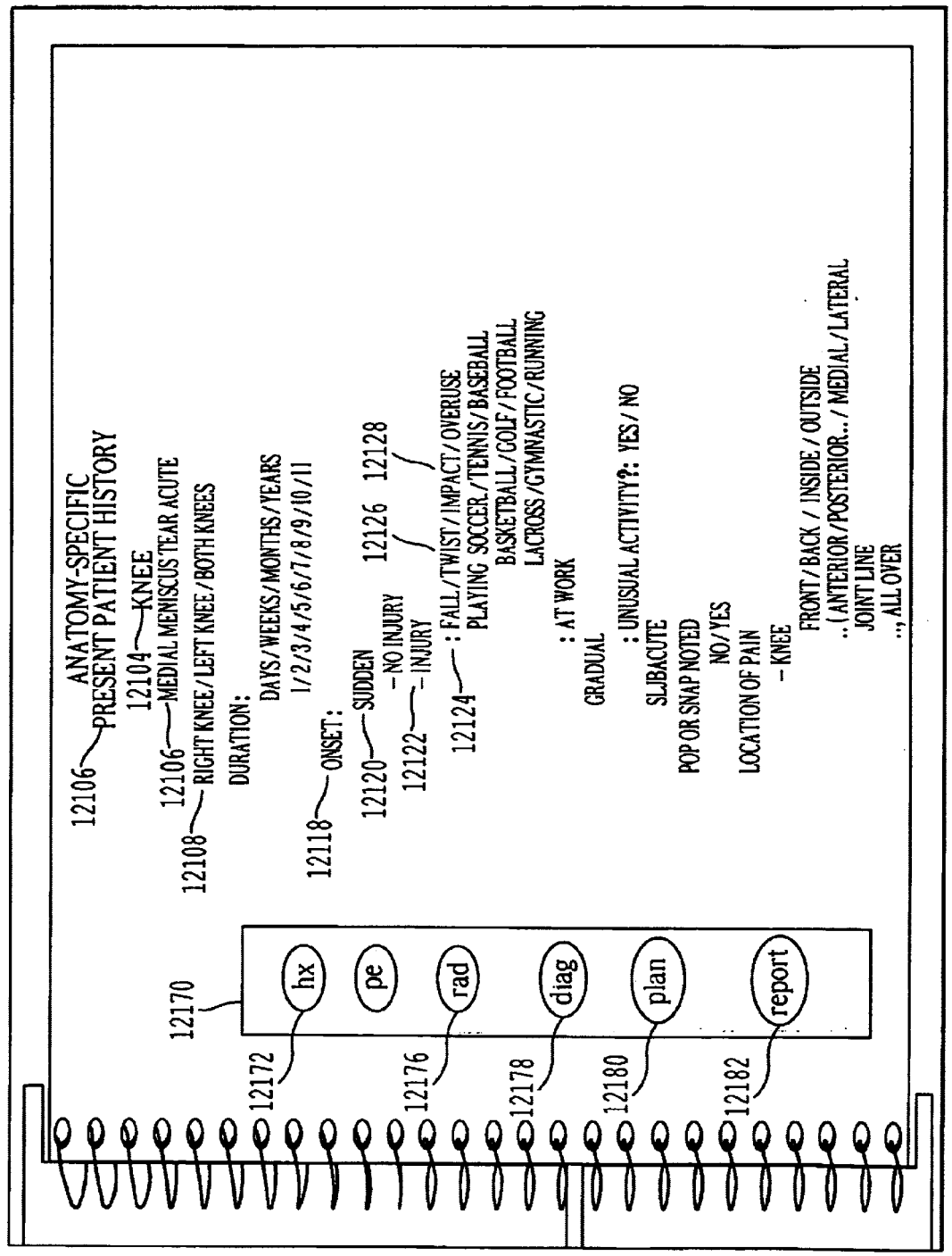
Figure 12C:
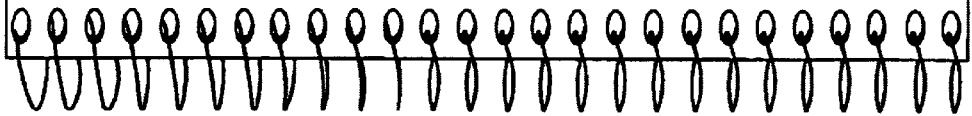
Figure 12F:
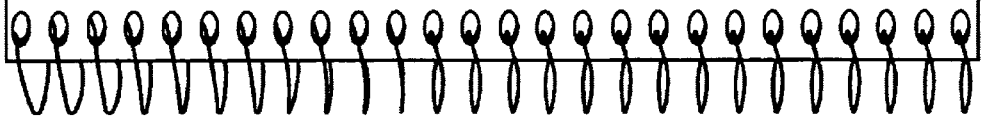
Figure 16:
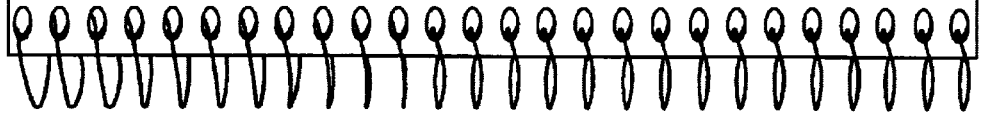

Referring now to FIG. 12A, an exemplary embodiment of a diagnostic specific template for a "medial meniscus tear" 12102 is illustrated. The preferred embodiment of the diagnostic specific template of the present invention is depicted in a manner suitable for display on a graphical user interface. The exemplary display has a tool bar 12170 which allows the user of the present invention to navigate between specific areas and layers of the diagnostic specific template such as the history area 12172, the physical examination area, the radiologic area 12176, the diagnostic area 12178, a treatment plan area 12180, and a report area 12182, as well as other relevant areas in the diagnostic specific template.

As depicted in the exemplary embodiment in FIG. 12A, a present patient history data schematic is represented which contains pertinent positive and negative findings for a medial meniscus tear injury. The items which are highlighted are the items which have the highest probability of being associated with the injury. The highlighted fields included in the present embodiment, including "onset" 12118, "sudden" 12120, "injury" 12122, "fall" 12124, "twist" 12126, and the other highlighted fields depicted in FIG. 12A, represent the most likely positive and negative findings for the injury "medial meniscus tear" 12106 to the "knee" 12104.

The schematic representation of clinical findings in FIG. 12A becomes the data model for the representation of the same clinical findings in FIG. 13C. In the exemplary embodiment of the present invention depicted in FIG. 13C, the present history data schematic illustrated in FIG. 12A has been automatically compiled into a text summary of the clinical findings.

In the example text summary of the present history, field 13122 "immediate pain" corresponds to the schematic data representation of the clinical finding illustrated in FIG. 12A by onset 12118 and sudden 12120.

Referring now to FIG. 12B a preferred embodiment of the schematic representation for the physical examination findings relevant to a medial meniscus tear is illustrated. The relevant positive findings are represented in schematic form in which the most probable finding is highlighted.

Further physical examination schematics are depicted in exemplary embodiments in FIGS. 12C, 12D, 12E and 12F. The physical examination schematics are a complete data model of the physical examination findings which are most likely to be associated with the medial meniscus tear diagnosis.

The graphics/icon modulated schematics feature of a preferred embodiment of the present invention will now be described.

Referring again to FIG. 12A, a user of the present invention may focus on a particular item of the schematic such as item 12108. The item selected may then be modified by either clicking with the mouse on the field desired or by inputting text data from keyboard or other device. Data input is also possible in a preferred embodiment of the present invention using voice activated means and voice recognition software, such as that described in Gralla, P., Id. pages 274–275.

For example, if the physician using a system of the present invention prefers to modify a particular field, such as the "onset" field 12118 in FIG. 12A, he may use the mouse device to navigate from the "onset" field 12118 to the "injury" field 12122, for example, and then use the mouse to select a non-default item such as "impact" 12128 instead of the default item "fall" 12124 for the "cause of injury" 12122. The physician user may also override any field, such as the "injury" field 12122, by using an input device to input specific text. The newly entered text may then be saved in the database for future use the next time the diagnostic specific template is invoked. Thus, the preferred embodiment of the present invention achieves easy user modifiability of all of the data items of the data schematic.

The modified data items in the data schematic will then be compiled into text reports in the same manner as the default data items of the data schematic or any of the other pre-populated items of the data schematic. Thus, the modifications made by the user are immediately reflected in the text report output.

FIG. 13B illustrates an exemplary embodiment of the present invention of a text summary which is automatically derived from the physical examination data schematic illustrated in FIGS. 12A–12F. For example, the fields "normal skin color" 13210, "deformity" 13214, "moderate" 13218, and "diffuse swelling" 13220 are compiled from the diagnostic data schematic fields of FIG. 12B "color" 12208, "normal" 12210, "clinical deformity" 12222, "mod" 12226, and "swelling" 12234, "diffuse" 12250, respectively. The fields of the text summary of FIG. 13B are end-user modifiable in the present invention, for example, by text or voice input.

FIGS. 14–17 illustrate exemplary embodiments of the present invention for x-ray report diagnostic specific pre-populated templates relevant to a medial meniscus tear. After having read the patient's x-rays, the physician will select the appropriate diagnostic specific template based on the patient's age and the x-ray clinical findings. For example, FIG. 15 shows an exemplary data schematic 40 appropriate for a patient of age over 65 years and mild DJD medial.

Figure 18:
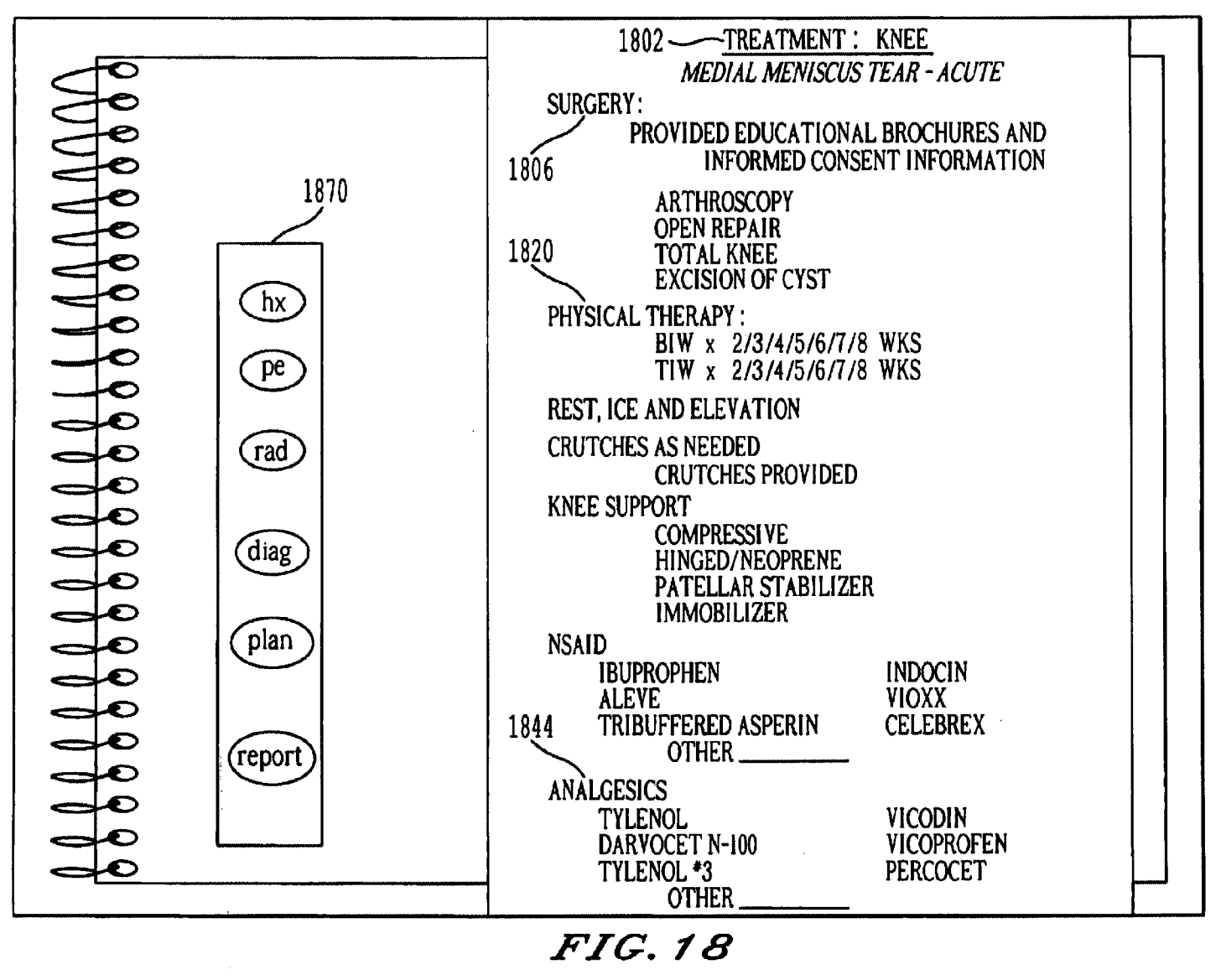

FIG. 18 is an exemplary embodiment of the present invention of the data schematic associated with treatment of a "medial meniscus tear-acute" 1802. The tool bar 1870 may be used to navigate between the various areas and functions of the present invention. Exemplary pre-populated data fields in the schematic are "surgery" 1806, "physical therapy" 1820, and "analgesics" 1844. The data schematic representation of the treatment for a medial meniscus tear illustrates highlighted fields which are associated with the most probable treatment modalities associated with a medial meniscus tear.

FIG. 19 illustrates an exemplary embodiment of the present invention a "summary text history of present illness and physical examination" 1902 associated with a "medial meniscus tear-acute" 1904. The exemplary text summary 1920 is derived from the exemplary data schematics, constituting the exemplary diagnostic specific template for a medial meniscus tear, illustrated in FIGS. 12A–12 F, FIGS. 14–17, and FIG. 18. The fields of the text summary of FIG. 19 are end-user modifiable in the present invention, for example, by text or voice input.

The exemplary text report of FIG. 19, constituting an electronic medical record, is suitable for immediate use, for example, by payment and audit entities, and may be communicated, for example, throughout the distributed computing environment illustrated by FIG. 9.

Numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the united states is:

1. A patient encounter electronic medical record apparatus comprising:
   a processor;
   an input interface configured to receive data input by a physician and an output interface coupled to said processor;
   a memory; and
   a plurality of diagnosis specific pre-populated templates stored in said memory and accessible by said processor, default entries in said diagnosis specific pre-populated templates being changeable to alternate values by said physician, said default entries being associated with a pre-determined diagnosis;
   wherein said user interface is configured to receive an input by said physician after said physician has made a diagnosis to select a subset of said diagnosis specific pre-populated templates that correspond with the diagnosis made by the physician and said processor is configured to produce an electronic medical record from said subset of diagnosis specific pre-populated templates.

2. The apparatus of claim 1, wherein said input interface includes a graphical user interface.

3. The apparatus of claim 1, wherein said output interface includes a graphical user interface.

4. The apparatus of claim 1, wherein said processor is a component of a distributed computing system.

5. The apparatus of claim 1, wherein said plurality of diagnosis specific pre-populated templates are configured for at least one of a drilldown logic and a rollup logic.

6. The apparatus of claim 1, wherein said plurality of diagnosis specific pre-populated templates include graphics modulated schematics.

7. The apparatus of claim 1, wherein said diagnosis specific pre-populated templates are derived from at least one of a selective specialty specific database and an anatomic specific database.

8. The apparatus of claim 1, wherein said diagnosis specific pre-populated templates are end-user modifiable.

9. The apparatus of claim 1, wherein said input interface is configured to convert voice input into text via a speech recognition mechanism.

10. The apparatus of claim 1, wherein said input interface is configured to receive data of at least one of a digital image input, a digital x-ray input, and a wireless device input.

11. The apparatus of claim 1, wherein said plurality of diagnosis specific prepopulated templates are configured for at least one of E/M documentation, x-rays, diagnostic studies, prescriptions, and reports.

12. The apparatus of claim 4, wherein said distributed computing environment comprises at least one of a payment system and an audit system.

13. The apparatus of claim 4, wherein said distributed computing environment comprises at least one of a Wide Area Network, a Local Area Network, and a Wireless Network.

14. A patient encounter electronic medical record apparatus comprising:
   a processor;
   inputting means for receiving data input by a physician and outputting means for outputting data, said inputting means and said outputting means coupled to said processor;

memory means for storing data; and a plurality of diagnosis specific pre-populated template means for structuring data stored in said memory means and accessible by said processor means, default entries in said diagnosis specific pre-populated template means being changeable to alternate values by said physician, said default entries being associated with a predetermined diagnosis;

wherein said inputting means is configured to receive an input by said physician after said physician has made a diagnosis to select a subset of said diagnosis specific pre-populated template means that correspond with the diagnosis made by the physician, and said processor produces an electronic medical record from said plurality of diagnosis specific pre-populated template means.

15. The apparatus of claim 14, wherein said inputting means includes a graphical interface.

16. The apparatus of claim 14, wherein said outputting means includes a graphical interface.

17. The apparatus of claim 14, wherein said processing means is a component of a distributed computing means.

18. The apparatus of claim 14, wherein said plurality of diagnosis specific prepopulated template means are configured for at least one of a drilldown logic and a rollup logic.

19. The apparatus of claim 14, wherein said plurality of diagnosis specific prepopulated template means includes graphics modulated schematic means.

20. The apparatus of claim 14, wherein said diagnosis specific pre-populated template means are derived from at least one of a selective specialty specific database and an anatomic specific database.

21. The apparatus of claim 14, wherein said diagnosis specific pre-populated template means is end-user modifiable.

22. The apparatus of claim 14, wherein said inputting means is configured for receiving voice input and means for converting speech into text.

23. The apparatus of claim 14, wherein said inputting means is configured for receiving at least one of a digital image, a digital x-ray input, and data from a wireless device.

24. The apparatus of claim 14, wherein said plurality of diagnosis specific prepopulated template means are configured for receiving at least one data from E/M documentation, an x-ray record, a diagnostic study, a prescription, and report.

25. The apparatus of claim 17, wherein said processor comprises at least one of a means for making a payment and a means for conducting an audit.

26. The apparatus of claim 17, wherein said processor is a component of at least one of a Wide Area Network, a Local Area Network, and a Wireless Network.

27. A patient encounter electronic medical record computer product comprising:

a memory configured to hold computer-readable instructions; and a plurality of diagnosis specific pre-populated templates stored in said memory and accessible by said processor, default entries in said diagnosis specific pre-populated templates being changeable to alternate values by said physician, said default entries being associated with a predetermined diagnosis;

wherein said user interface is configured to receive an input by said physician after said physician has made a diagnosis to select a subset of said diagnosis specific pre-populated templates that correspond with the diagnosis made by the physician, and wherein said processor is configured to produce an electronic medical record from said subset of diagnosis specific pre-populated templates.

28. The computer product of claim 27, wherein said input interface includes a graphical user interface.

29. The computer product of claim 27, wherein said output interface includes a graphical user interface.

30. The computer product of claim 27, wherein said processor is a component of a distributed computing system.

31. The computer product of claim 27, wherein said plurality of diagnosis specific pre-populated templates are configured for at least one of a drilldown logic and a rollup logic.

32. The computer product of claim 27, wherein said at least one of a plurality of diagnosis specific pre-populated templates comprises graphics modulated schematics.

33. The computer product of claim 27, wherein said diagnosis specific pre-populated templates are derived from at least one of a selective specialty specific database and an anatomic specific database.

34. The computer product of claim 27, wherein said diagnosis specific pre-populated templates are end-user modifiable.

35. The computer product of claim 27, wherein said input interface is configured to convert voice into text via a speech recognition mechanism.

36. The computer product of claim 27, wherein said input interface is configured to receive data of at least one of a digital image, a digital x-ray, and a wireless device.

37. The computer product of claim 27, wherein said plurality of diagnosis specific pre-populated templates are configured to include data from at least one of E/M documentation, x-rays, diagnostic studies, prescriptions, and reports.

38. The computer product of claim 30, wherein said distributed computing system comprises at least one of a payment system and an audit system.

39. The computer product of claim 30, wherein said distributed computing system comprises at least one of a Wide Area Network, a Local Area Network, and a Wireless Network.

40. A method for recording a patient encounter electronic medical record, comprising the steps of:

holding a plurality of diagnosis specific pre-populated templates with default entries in a memory and accessible by a processor;

making a diagnosis by a physician;

retrieving a subset of the plurality of diagnosis specific pre-populated templates that correspond with the diagnosis made by the physician, said retrieving step being performed after said step of making a diagnosis;

verifying said default entries and changing as necessary said default entries in said subset of the diagnosis specific pre-populated templates by a physician input; and producing an electronic medical record from said subset of diagnosis specific pre-populated templates and entries associated therewith, after said verifying step.

41. The method of claim 40, wherein said retrieving step includes at least one of a drilldown processing step and a rollup processing step.

42. The method of claim 40, wherein said retrieving step includes graphically modulating schematic data.

43. The method of claim 40, further comprising:

deriving said diagnosis specific pre-populated templates from at least one of a selective specialty specific database and an anatomic specific database.

\* \* \* \* \*